United States Patent
Abdullah et al.

(10) Patent No.: US 12,209,126 B2
(45) Date of Patent: Jan. 28, 2025

(54) TREATMENT OF CANCER

(71) Applicants: MEDIMMUNE LIMITED, Cambridge (GB); INNATE PHARMA, Marseilles (FR)

(72) Inventors: Shaad Essa Abdullah, Gaithersburg, MD (US); Ashok Kumar Gupta, Gaithersburg, MD (US); Xuyang Song, Gaithersburg, MD (US)

(73) Assignees: MEDIMMUNE LIMITED, Cambridge (GB); INNATE PHARMA, Marseilles (FR)

( * ) Notice: Subject to any disclaimer, the term of this patent is extended or adjusted under 35 U.S.C. 154(b) by 1104 days.

(21) Appl. No.: 17/054,920

(22) PCT Filed: May 14, 2019

(86) PCT No.: PCT/EP2019/062305
§ 371 (c)(1),
(2) Date: Nov. 12, 2020

(87) PCT Pub. No.: WO2019/219658
PCT Pub. Date: Nov. 21, 2019

(65) Prior Publication Data
US 2021/0253694 A1 Aug. 19, 2021

Related U.S. Application Data

(60) Provisional application No. 62/671,521, filed on May 15, 2018.

(51) Int. Cl.
*C07K 16/28* (2006.01)
*A61P 35/00* (2006.01)

(52) U.S. Cl.
CPC .......... *C07K 16/2803* (2013.01); *A61P 35/00* (2018.01); *C07K 16/2818* (2013.01); *C07K 16/2827* (2013.01); *C07K 2317/565* (2013.01)

(58) Field of Classification Search
CPC ............ C07K 16/2803; C07K 16/2818; C07K 16/2827; C07K 2317/565; C07K 2317/24; C07K 2317/21; C07K 2317/76; A61P 35/00; A61K 2039/507; A61K 2039/545; A61K 45/06; A61K 2300/00
See application file for complete search history.

(56) References Cited

U.S. PATENT DOCUMENTS

| | | | |
|---|---|---|---|
| 8,206,709 B2 | 6/2012 | Spee et al. |
| 8,796,427 B2 | 8/2014 | Spee et al. |
| 8,901,283 B2 | 12/2014 | Spee et al. |
| 8,993,319 B2 | 3/2015 | Moretta et al. |
| 9,422,368 B2 | 8/2016 | Spee et al. |
| 9,512,228 B2 | 12/2016 | Soederstroem et al. |
| 9,683,041 B2 | 6/2017 | Spee et al. |
| 10,160,810 B2 | 12/2018 | Moretta et al. |
| 10,329,348 B2 | 6/2019 | Andre et al. |
| 10,676,523 B2 | 6/2020 | Andre et al. |
| 10,709,782 B2 | 7/2020 | Parshad |
| 10,711,063 B2 | 7/2020 | Andre et al. |
| 10,870,700 B2 | 12/2020 | Andre et al. |
| 11,225,519 B2 | 1/2022 | Andre et al. |
| 11,572,410 B2 | 2/2023 | Andre et al. |
| 2011/0229486 A1 | 9/2011 | Moretta et al. |
| 2015/0132316 A1 | 5/2015 | Moretta et al. |
| 2017/0073417 A1 | 3/2017 | Soederstroem et al. |
| 2017/0253658 A1 | 9/2017 | Van Der Burg et al. |
| 2017/0281809 A1 | 10/2017 | Spee et al. |
| 2019/0248896 A1 | 8/2019 | Spee et al. |
| 2020/0109206 A1 | 4/2020 | Soederstroem et al. |
| 2020/0299383 A1 | 9/2020 | Andre et al. |
| 2021/0061909 A1 | 3/2021 | Boyer-Chammard et al. |
| 2021/0122821 A1 | 4/2021 | Andre et al. |
| 2021/0238285 A1 | 8/2021 | Andre et al. |

FOREIGN PATENT DOCUMENTS

| | | | | |
|---|---|---|---|---|
| WO | WO-2016032334 A1 * | 3/2016 | ............. | A61K 35/17 |
| WO | WO-2016041945 A1 * | 3/2016 | ........... | A61K 39/395 |
| WO | 2017106656 A1 | 6/2017 | | |
| WO | 2017125532 A1 | 7/2017 | | |

OTHER PUBLICATIONS

Denis C et al. P191 NK, T cells and IFN-gamma are required for the anti-tumor efficacy of combination-treatment with NKG2A and PD-1/PD-L1 checkpoint inhibitors in preclinical models. Journal for ImmunoTherapy of Cancer 2016, 4(Suppl 1):73 p. 108 (Year: 2016).*

Zeestraten ECM et al. Combined analysis of HLA class I, HLA-E and HLA-G predicts prognosis in colon cancer patients. Br J Cancer. Jan. 2, 20141; 110(2): 459-468 (Year: 2014).*

Zeinalian M et al. Clinical Aspects of Microsatellite Instability Testing in Colorectal Cancer. (Adv Biomed Res. 2018 7: 28) (Year: 2018).*

Levy EM et al. Human leukocyte antigen-E protein is overexpressed in primary human colorectal cancer. Intl J of Oncology 2008 32: 633-641 (Year: 2008).*

Ahmed D et al. Epigenetic and genetic features of 24 colon cancer cell lines. Oncogenesis. Sep. 2013; 2(9): e71. (Year: 2013).*

(Continued)

*Primary Examiner* — Julie Wu
*Assistant Examiner* — John J Skoko, III
(74) *Attorney, Agent, or Firm* — SALIWANCHIK, LLOYD & EISENSCHENK

(57) ABSTRACT

The present invention relates to the use of NKG2A-neutralizing agents and PD-1 neutralizing agents to treat cancers, notable cancers that are not characterized by DNA mismatch repair deficiency. Provided are methods of treatment of a cancer, as well as compositions and kits useful for treating a cancer that is not characterized by DNA mismatch repair deficiency.

18 Claims, 2 Drawing Sheets
Specification includes a Sequence Listing.

(56) References Cited

OTHER PUBLICATIONS

Franksson L et al. Tumorigenicity conferred to lymphoma mutant by major histocompatibility complex-encoded transporter gene. (J Exp Med. Jan. 1, 1993; 177(1): 201-205). (Year: 1993).*

Mlecnik B et al. Integrative Analyses of Colorectal Cancer Show Immunoscore Is a Stronger Predictor of Patient Survival Than Microsatellite Instability. (Immunity 2016 44(3) 698-711) (Year: 2016).*

Le DT et al. PD-1 Blockade in Tumors with Mismatch-Repair Deficiency. (N Engl J Med 2015;372:2509-2520 (Year: 2015).*

Mayer et al., Randomized Trial of TAS-102 for Refractory Metastatic Colorectal Cancer. (NEJM 2015 372:1909-1919) (Year: 2015).*

Grothey et al. Regorafenib monotherapy for previously treated metastatic colorectal cancer (CORRECT): an international, multicentre, randomised, placebo-controlled, phase 3 trial. (Lancet 2013, 381(9863): 303-312) (Year: 2013).*

Segal, Nell Howard, et al., "First-in-human dose escalation of monalizumab plus durvalumab, with expansion in patients with metastatic microsatellite-stable colorectal cancer", Journal of Clinical Oncology, Jun. 1, 2018, 36(15), suppl. 3540.

Claims as filed in U.S. Appl. No. 18/164,649, filed Feb. 6, 2023, p. 1.

Claims as filed in U.S. Appl. No. 17/768,484, filed Apr. 13, 2022, pp. 1-4.

Schilling, B. et al. "IRX-2, a novel immunotherapeutic, enhances and protects NK-cell functions in cancer patients" *Cancer Immunol Immunother*, 2012, pp. 1395-1405, vol. 61.

Vermorken, J. B et al. "Cisplatin, Fluorouracil, and Docetaxel in Unresectable Head and Neck Cancer" *The New England Journal of Medicine*, Oct. 25, 2007, pp. 1695-1704, vol. 357.

Therapeutic Antibody Engineering, Chapter 10, "Antibody Fc engineering for optimal antibody performance", eds. Willaim R. Strohl, Lila M. Strohl, Woodhead Publishing, 2012, pp. 225-249 and pp. 459-595.

Shemirani, A. I et al. "Simplified MSI Marker Panel for Diagnosis of Colorectal Cancer" *Asian Pacific Journal of Cancer Prevention*, 2011, pp. 2101-2104, vol. 12.

Dudley, J. C et al. "Microsatellite Instability as a Biomarker for PD-1 Blockade" *Clinical Cancer Research*, Feb. 15, 2016, pp. 813-820, vol. 22, No. 4.

Llosa, N. J. et al. "The Vigorous Immune Microenvironment of Microsatellite Instable Colon Cancer Is Balanced by Multiple Counter-Inhibitory Checkpoints" *Cancer Discovery*, Jan. 2015, pp. 43-51.

Eugene, J. et al. "Abstract LB-142: CD94/NKG2A$^+$tumor-infiltrating lymphocytes in a context of HLA-E overexpression could be a promising new druggable inhibitory immune checkpoint in colorectal adenocarcinomas" Cancer Research, Jul. 1, 2018, pp. 1-2, vol. 78, Issue 13_Supplement, LB-142, pp. 1-2.

* cited by examiner

TREATMENT OF CANCER

CROSS-REFERENCE TO RELATED APPLICATIONS

This application is a U.S. National Stage application of International Application No. PCT/EP2019/062305, filed on May 14, 2019, said International Application No. PCT/EP2019/062305 claims benefit under 35 U.S.C. § 119 (e) of the U.S. Provisional Application No. 62/671,521, filed May 15, 2018. Each of the above listed applications is incorporated by reference herein in its entirety for all purposes.

REFERENCE TO THE SEQUENCE LISTING

This application incorporates by reference a Sequence Listing submitted with this application as text file entitled NKG2A-114-WO-PCT_Sequence_Listing.txt, created on Jun. 9, 2020, and having a size of 57,707 kilobytes.

FIELD OF THE INVENTION

This invention relates to the use of NKG2A-neutralizing agent and PD-1 neutralizing agent to treat cancer, notably cancer that is not characterized by DNA mismatch repair deficiency. Included is treatment of MSS cancer. The invention is particularly useful for treating advanced recurrent or metastatic colorectal cancer.

BACKGROUND OF THE INVENTION

NK cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46. These receptors are members of the Ig superfamily, and their cross-linking, induced by specific monoclonal antibodies, leads to a strong NK cell activation resulting in increased intracellular $Ca^{++}$ levels, triggering of cytotoxicity, and lymphokine release, and an activation of NK cytotoxicity against many types of target cells.

CD94/NKG2A is an inhibitory receptor found on subsets of lymphocytes. CD94/NKG2A restricts cytokine release and cytotoxic responses of certain lymphocytes towards cells expressing the CD94/NKG2A-ligand HLA-E. HLA-E has also been found to be secreted in soluble form by certain tumor cells and activated endothelial cells. Antibodies that inhibit CD94/NKG2A signalling may increase the cytokine release and cytolytic activity of lymphocytes towards HLA-E positive target cells, such as responses of CD94/NKG2A-positive NK cells towards HLA-E expressing tumor cells or virally infected cells. Neutralizing anti-NKG2A antibodies may therefore be useful in the treatment of cancer.

Colorectal cancer (CRC) accounts for 10%-15% of all cancers and is the leading cause of cancer deaths in the Western world. Standard of care for treatment of metastatic CRC (mCRC) remains the use of cytotoxic agents. More recently, immunotherapeutic agents have been tested in CRC. Le et al. (N Engl J Med. 2015; 372:2509-2520) conducted a phase 2 clinical study in CRC with pembrolizumab, an anti-programmed death 1 immune checkpoint inhibitor, finding that the immune-related objective response rate and immune-related PFS rate were 40% (4 of 10 patients) and 78% (7 of 9 patients) for MSI-H CRCs and 0% (0 of 18 patients) and 11% (2 of 18 patients) for microsatellite stable/proficient MSS CRCs, respectively. Only 1 of 10 patients with MSI-H CRC experienced disease progression, as compared to 11/18 MSS CRC patients.

Unfortunately, chemotherapeutic agents and/or targeted therapies do not provide sufficient and/or lasting anti-tumor responses patients having non-MSI-H CRC. There is thus a need in the art for improved benefit to patients treated without DNA repair deficiencies.

SUMMARY OF THE INVENTION

The present invention arises, inter alia, from the observation that human patients with MSS-CRC showed promising anti-tumor responses when treated with the NKG2A-neutralizing agent monalizumab and the PD-1-neutralizing agent durvalumab. While PD-1-neutralizing agents had been thought not well suited for MSS-CRC, it has been surprisingly found that the combination of these two agents could be beneficial for treating MSS-CRC. Without willing to be bound by theory, it could be that neutralization of the HLA-E/NKG2A axis could render MSS-CRC tumors sensitive to recognition and/or lysis by the host immune system.

In one aspect, the present invention provides methods of treating and/or preventing a cancer and/or eliciting an anti-tumor immune response in an individual in need thereof, wherein said individual has a non-MSI-High tumor, comprising treating said individual with an agent that neutralizes the inhibitory receptor NKG2A and an agent that neutralizes PD-1. In one embodiment, the tumor is MSI-Low. In another embodiment, the tumor is MSS. In one embodiment, the cancer or tumor is colorectal cancer (CRC), optionally advanced recurrent or metastatic colorectal cancer (mCRC).

In one aspect, the present invention provides methods of treating and/or preventing a cancer and/or eliciting an anti-tumor immune response in an individual in need thereof, wherein said individual has a tumor that is not DNA mismatch repair (MMR) defective, comprising treating said individual with an agent that neutralizes the inhibitory receptor NKG2A and an agent that neutralizes PD-1. In one embodiment, the tumor is MSI-Low. In another embodiment, the tumor is MSS. In one embodiment, the cancer or tumor is colorectal cancer (CRC), optionally advanced recurrent or metastatic colorectal cancer (mCRC).

In one aspect, the present invention provides methods of treating a cancer and/or eliciting an anti-tumor immune response in an individual in need thereof, wherein said individual has advanced recurrent or metastatic colorectal cancer, optionally metastatic colorectal cancer, that is not MSI-High (MSI-H) comprising treating said individual with an agent that neutralizes the inhibitory receptor NKG2A and an agent that neutralizes PD-1.

In one aspect, the present invention provides methods of treating a cancer and/or eliciting an anti-tumor immune response in an individual in need thereof, wherein said individual has advanced recurrent or metastatic colorectal cancer, optionally metastatic colorectal cancer, that is microsatellite instability-low (MSI-Low) or microsatellite stable (MSS), comprising treating said individual with an agent that neutralizes the inhibitory receptor NKG2A and an agent that neutralizes PD-1.

In one embodiment, provided is a method for treating or preventing a cancer, optionally a CRC or mCRC, in an individual comprising: (i) identifying an individual who has a tumor that is not DNA mismatch-repair defective, and (ii) administering to the individual an effective amount of agent that neutralizes the inhibitory receptor NKG2A and an effective amount of agent that neutralizes PD-1.

In one embodiment, provided is a method for treating or preventing a cancer, optionally a CRC or mCRC, in an individual comprising: (i) identifying an individual who has a tumor that is not a MSI-High tumor and (ii) administering to the individual an effective amount of agent that neutralizes the inhibitory receptor NKG2A and an effective amount of agent that neutralizes PD-1.

In one embodiment, provided is a method for treating or preventing a cancer, optionally a CRC or mCRC, in an individual comprising: (i) identifying an individual who has a tumor that is a MSS tumor and (ii) administering to the individual an effective amount of agent that neutralizes the inhibitory receptor NKG2A and an effective amount of agent that neutralizes PD-1.

In another embodiment, provided is a method for determining whether an individual having a cancer, optionally a CRC or mCRC, will derive particular benefit from, be responsive to and/or suitable for treatment with an agent that neutralizes the inhibitory receptor NKG2A and an agent that neutralizes PD-1, the method comprising determining whether said individual has a tumor that is DNA mismatch-repair defective, wherein a determination that the tumor is not DNA mismatch-repair defective indicates that the individual will derive particular benefit from, be responsive to and/or suitable for treatment with an agent that neutralizes the inhibitory receptor NKG2A and an agent that neutralizes a human PD-1 polypeptide.

In another embodiment, provided is a method for determining whether an individual having a cancer, optionally a CRC or mCRC, will derive particular benefit from, be responsive to and/or suitable for treatment with an agent that neutralizes the inhibitory receptor NKG2A and an agent that neutralizes PD-1, the method comprising determining whether said individual has a tumor that lacks microsatellite instability (e.g. the individual has a MSS tumor), wherein a determination that the tumor lacks microsatellite instability (e.g. the individual has a MSS tumor) indicates that the individual will derive particular benefit from, be responsive to and/or suitable for treatment with an agent that neutralizes the inhibitory receptor NKG2A and an agent that neutralizes a human PD-1 polypeptide.

Microsatellite instability is the condition of genetic hypermutability that results from impaired DNA mismatch repair (MMR). The presence of MSI represents phenotypic evidence that MMR is not functioning normally. In most cases, the genetic basis for instability in MSI tumors is an inherited germline alteration in any one or more of the five human MMR genes: MSH2, MLH1, MSH6, PMS2, and PMS1. Thus, microsatellite instability in a tumor can be determined by assessing microsatellite markers and/or MMR genes.

In one embodiment, the step of identifying an individual whose tumor does not have microsatellite instability (e.g. whose tumor is microsatellite stable (MSS)) comprises: (a) obtaining a biological sample from the individual comprising tumor cells (e.g. comprising obtaining a biopsy), (b) determining the microsatellite status of tumor cells within the biological sample. A finding that the individual has a tumor that is not characterized by microsatellite instability (e.g., the tumor is MSS, the tumor is characterized by microsatellite stability) indicates that the individual can be advantageously treated with an agent that neutralizes the inhibitory receptor NKG2A and an agent that neutralizes PD-1.

In one embodiment, the step of determining the microsatellite status of tumor cells comprises detecting an alteration in expression of a DNA mismatch repair (MMR) protein in the tumor cells, optionally wherein the MMR protein is selected from MSH2, MLH1, MSH6, PMS2, and PMS1, optionally wherein the MMR gene or protein is selected from MSH2, MLH1, MSH6 and PMS2. In one embodiment, a finding that the individual has a tumor characterized by decreased or absence of at least one MMR protein indicates that the tumor is characterized by microsatellite instability. An individual whose tumor does not have decreased or absence of at least one MMR protein can be specified as indicating that the tumor is characterized by microsatellite stability (e.g. MSS) and can be advantageously treated with an agent that neutralizes the inhibitory receptor NKG2A and an agent that neutralizes PD-1. Decrease in MMR protein can for example be assessed according to standard methods and guidelines for assessing DNA mismatch repair deficiency. Optionally a decrease in expression of a MMR protein may correspond to a decrease compared to a reference value associated with MSS; optionally a decrease in expression of a MMR protein corresponds to a reference value associated with MSI. Alternatively, the decrease of at least one MMR protein can be evaluated by comparison to a reference value that can be, for instance, the level of the same MMR protein(s) measured in a healthy tissue of the same individual, or the level of the same MMR protein(s) measured in a tumor sample of the same individual analyzed at a different period of time, or the average level of the same MMR protein(s) in biological samples from healthy individuals such as individuals not suffering from cancer.

In one embodiment, the step of determining the microsatellite status of tumor cells comprises detecting alterations in microsatellite markers or microsatellite marker panels. Optionally, alterations are detected in one or more microsatellite markers selected from the group consisting of BAT-25, BAT-26, NR-21, NR-24, MONO27, D5S346, D2S123 and D17S250, more particularly from the group consisting of BAT-25, BAT-26, NR-21, NR-24, and MONO27. An individual whose tumor does not have high-frequency microsatellite instability indicates that the tumor is characterized by microsatellite stability (MSS) or low microsatellite instability (MSI-Low) and can be advantageously treated with an agent that neutralizes the inhibitory receptor NKG2A and an agent that neutralizes PD-1.

In one embodiment, the agent that neutralizes the inhibitory receptor NKG2A is a protein (e.g. an antibody) that neutralizes the inhibitory activity of the human NKG2A polypeptide, optionally by inhibiting the interaction between human HLA-E and human NKG2A proteins. In one embodiment, the agent that neutralizes the inhibitory receptor NKG2A is a protein (e.g. an antibody) that binds human NKG2A polypeptide and neutralizes the inhibitory activity of the human NKG2A polypeptide, with or without inhibiting the interaction between human HLA-E and human NKG2A proteins. In one embodiment, the agent that neutralizes the inhibitory receptor NKG2A is a protein (e.g. an antibody) that binds the human HLA-E polypeptide and inhibits the interaction between human HLA-E and human NKG2A proteins.

In one embodiment, the agent that neutralizes a human PD-1 polypeptide is an anti-PD-1 or anti-PDL-1 antibody that neutralizes the inhibitory activity of PD-1. The individual can be specified to be a human.

In one embodiment, provided is a method of increasing the activity and/or numbers of tumor-infiltrating CD8+ T cells and/or NK cells in an individual who has a tumor (e.g., a CRC, a mCRC) that is not characterized by defective DNA mismatch repair, the method comprising administering to the individual a therapeutically active amount of a compound that neutralizes the inhibitory receptor NKG2A and a therapeutically active amount of a compound that neutralizes PD-1 polypeptide.

In one embodiment, provided is a method of increasing the activity and/or numbers of tumor-infiltrating CD8+ T cells and/or NK cells in an individual who has a tumor (e.g., a CRC, a mCRC) that is not characterized by microsatellite instability (e.g. a cancer characterized as MSS), the method comprising administering to the individual a therapeutically active amount of a compound that neutralizes the inhibitory receptor NKG2A and a therapeutically active amount of a compound that neutralizes PD-1 polypeptide.

In one embodiment, provided is an agent that neutralizes NKG2A, optionally an anti-NKG2A antibody, for use in the treatment of colorectal cancer (e.g., mCRC) that is not characterized by microsatellite instability (e.g. a cancer characterized as MSS), wherein the agent that neutralizes NKG2A is administered in combination with an agent that neutralizes PD-1, optionally an anti-PD-1 or anti-PD-L1 antibody.

In one embodiment, provided is an agent that neutralizes a human PD-1 polypeptide, optionally an anti-PD-L1 antibody or an anti-PD-1 antibody, for use in the treatment of colorectal cancer (e.g., mCRC) that is not characterized by microsatellite instability (e.g. a cancer characterized as MSS), wherein the agent that neutralizes a human PD-1 polypeptide is administered in combination with an agent that neutralizes the inhibitory receptor NKG2A, optionally an anti-NKG2A antibody.

In one aspect of any embodiment herein, the individual has received prior treatment with radiotherapy, surgery, chemotherapy, and/or treatment with a biological agent.

These aspects are more fully described in, and additional aspects, features, and advantages will be apparent from, the description of the invention provided herein.

DETAILED DESCRIPTION

Definitions

Figure 1:
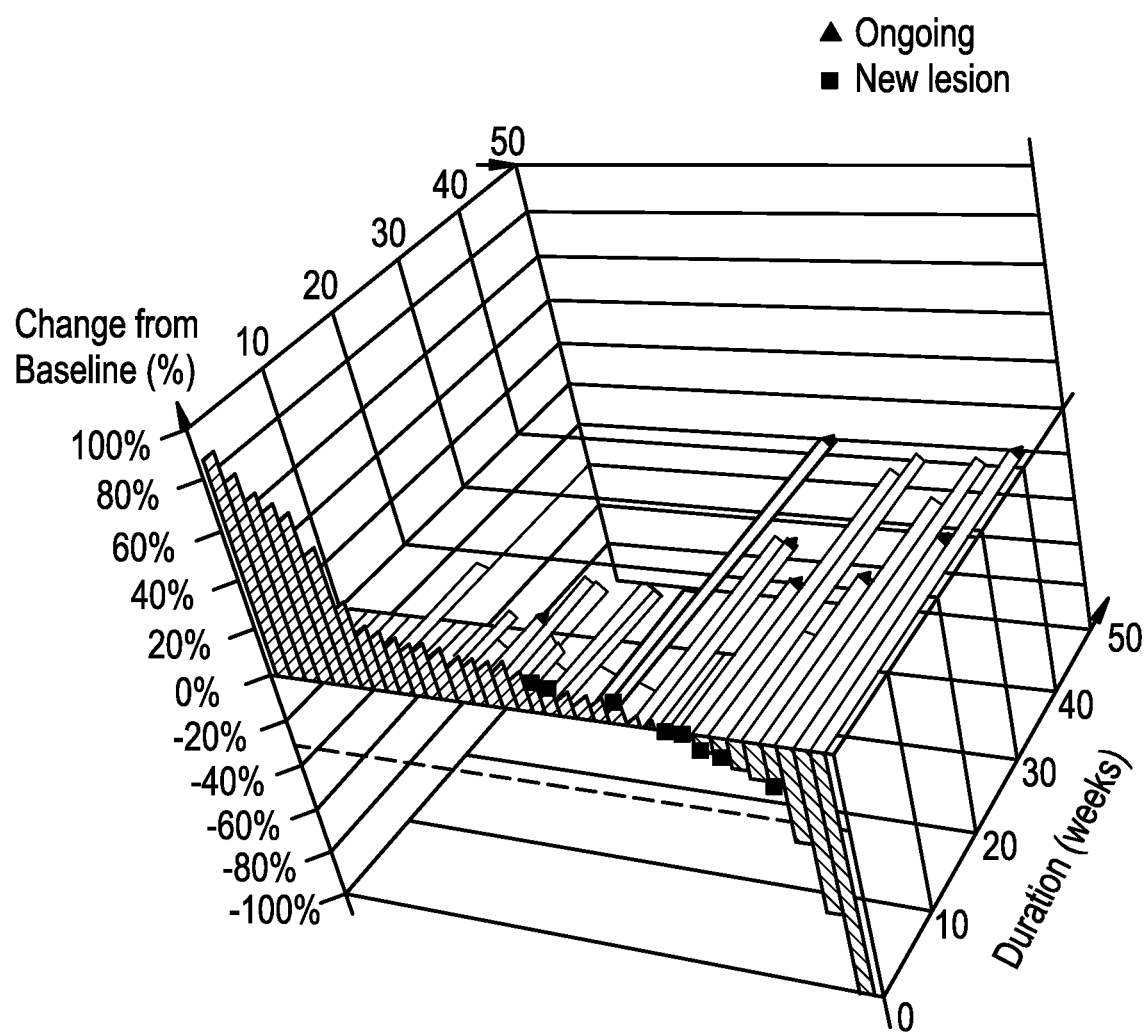
FIG. 1 is a 3D representation of the Best Change in Tumor Size from Baseline (in %, left-hand vertical axis) and Duration of Treatment Response in the Evaluable Population (in weeks, z axis) for each patient (horizontal axis) in the expansion cohort of the MSS-CRC trial.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Human NKG2A comprises 233 amino acids in 3 domains, with a cytoplasmic domain comprising residues 1-70, a transmembrane region comprising residues 71-93, and an extracellular region comprising residues 94-233, of the following sequence: MDNQGVIYSDLNLPPNPKRQQRKPKGNKSSILATE-QEITYAELNLQKASQDFQGNDKTYHC KDLPSA-PEKLIVGILGIICLILMASVVTIVVIP-STLIQRHNNSSLNTRTQKARHCGHCP EEWITYSNSCYYIGKERRTWEESLLACTSKNSSLL-SIDNEEEMKFLSIISPSSWIGVFRNSS HHPWVTMNGLAFKHEIKDSDNAELN-CAVLQVNRLKSAQCGSSIIYHCKHKL (SEQ ID NO: 1).

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g. such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein.

In the context of the present invention, "NKG2A-", or "CD94/NKG2A-", "positive lymphocyte", or "restricted lymphocyte", refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "NKG2A positive lymphocyte" also includes immortal cell lines of lymphoid origin (e.g. NKL, NK-92).

In the context of the present invention, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation that neutralizes NKG2A causes at least a 10% augmentation in the cytotoxicity of a CD94/NKG2A-restricted lymphocyte, optionally at least a 40% or 50% augmentation in said lymphocyte cytotoxicity, optionally at least a 70% augmentation in said lymphocyte cytotoxicity", optionally at least a 70% augmentation of NK cytotoxicity, and referring to the cytotoxicity assays described herewith. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E$^+$ LCL 721.221-Cw3 cells due to HLA-E-induced inhibitory signaling via CD94/NKG2A. When NK cells are pre-incubated with blocking anti-CD94/NKG2A antibodies described herewith in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 monoclonal antibody prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn., IFN-γ: OptEIA set, Pharmingen).

In one embodiment, provided is a method of increasing the activity and/or numbers of tumor-infiltrating CD8+ T cells and/or NK cells in an individual who has a tumor (e.g., a CRC, a mCRC) that is not characterized by defective DNA mismatch repair, the method comprising administering to the individual a therapeutically active amount of a compound that neutralizes the inhibitory receptor NKG2A and a therapeutically active amount of a compound that neutralizes PD-1 polypeptide.

In one embodiment, provided is a method of increasing the activity and/or numbers of tumor-infiltrating CD8+ T cells and/or NK cells in an individual who has a tumor (e.g., a CRC, a mCRC) that is not characterized by microsatellite instability (e.g. a cancer characterized as MSS), the method comprising administering to the individual a therapeutically active amount of a compound that neutralizes the inhibitory receptor NKG2A and a therapeutically active amount of a compound that neutralizes PD-1 polypeptide.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, e.g., arresting its development; or relieving the disease, e.g., causing regression of the disease and/or its symptoms or conditions such as improvement or remediation of damage, for example in a subject who has been diagnosed as having the disease. Optionally, treatment may cause (e.g. may be characterized as a method of causing) a decrease in tumor burden, a decrease in the size and/or number of lesions, a decrease or delay in the progression of cancer (e.g., an increase in progression-free survival), a delay or prevention of cancer metastasis and/or an increase in survival. Optionally, treatment may cause or provide (e.g. may be characterized as a method of causing or providing) stable disease, a partial response or a complete response in a subject, e.g. according to standard criteria, optionally RECIST criteria.

Whenever "treatment of cancer" or the like is mentioned with reference to a NKG2A neutralizing agent (e.g. antibody) and/or to a PD-1 neutralizing agent (e.g. antibody), are comprised:
  (a) a method of treatment of cancer, said method comprising the step of administering (for at least one treatment) an NKG2A neutralizing agent and a PD-1 neutralizing agent, (e.g., together or each separately in a pharmaceutically acceptable carrier material) to an individual, a mammal, especially a human, in need of such treatment, in a dose that allows for the treatment of cancer, (a therapeutically effective amount), optionally in a dose (amount) as specified herein;
  (b) the use of a NKG2A neutralizing agent and of a PD-1 neutralizing agent for the treatment of cancer;
  (c) a NKG2A neutralizing agent and a PD-1 neutralizing agent, for use in the treatment of cancer (especially in a human);

(d) a NKG2A neutralizing agent for use in the treatment of cancer (especially in a human), wherein said NKG2A neutralizing agent is administered in combination with a PD-1 neutralizing agent;
(e) a PD-1 neutralizing agent for use in the treatment of cancer (especially in a human), wherein said PD-1 neutralizing agent is administered in combination with a NKG2A neutralizing agent;
(f) the use of a NKG2A neutralizing agent and of a PD-1 neutralizing agent for the manufacture of a pharmaceutical preparation for the treatment of cancer,
(g) a method of using a NKG2A neutralizing agent and a PD-1 neutralizing agent for the manufacture of a pharmaceutical preparation for the treatment of cancer, comprising admixing a NKG2A neutralizing agent and/or a PD-1 neutralizing agent with a pharmaceutically acceptable carrier,
(h) a pharmaceutical preparation comprising an effective dose of a NKG2A neutralizing agent and/or of a PD-1 neutralizing agent that is appropriate for the treatment of cancer;
(i) any combination of (a), (b), (c), (d), (e), (f), (g), and (h), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. NKG2A for an anti-NKG2A antibody, PD-L1 for an anti-PD-L1 antibody, PD-1 for an anti-PD-1 antibody, as assessed using either recombinant forms of the proteins, epitopes therein, or native proteins present on the surface of isolated target cells. Competitive binding assays and other methods for determining specific binding are well known in the art. For example binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target. An agent that specifically binds NKG2A may bind NKG2A alone or NKG2A as a dimer with CD94.

When an antibody is said to "compete with" a particular monoclonal antibody, it means that the antibody competes with the monoclonal antibody in a binding assay using either recombinant molecules (e.g., NKG2A) or surface expressed molecules (e.g., NKG2A). For example, if a test antibody reduces the binding of an antibody having a heavy chain variable region of any of SEQ ID NOS: 4-8 and a light chain variable region of SEQ ID NO: 9 to a NKG2A polypeptide or NKG2A-expressing cell in a binding assay, the antibody is said to "compete" respectively with such antibody.

The term "affinity", as used herein, means the strength of the binding of an antibody to an epitope. The affinity of an antibody is given by the dissociation constant Kd, defined as [Ab]×[Ag]/[Ab−Ag], where [Ab−Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of monoclonal antibodies can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of monoclonal antibodies is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

NKG2A-Neutralizing Therapeutic Agents

The NKG2A neutralizing agent binds an extra-cellular portion of human CD94/NKG2A receptor or its ligand HLA-E and reduces the inhibitory activity of human CD94/NKG2A receptor expressed on the surface of a CD94/NKG2A positive lymphocyte. In one embodiment the agent competes with HLA-E in binding to CD94/NKG2A, i.e. the agent blocks the interaction between CD94/NKG2A and its ligand HLA-E. In another embodiment the agent binds NKG2A but does not compete with HLA-E in binding to CD94/NKG2A; i.e. the agent is capable of binding CD94/NKG2A simultaneously with HLA-E. In one embodiment, the agent is an antibody that binds to NKG2A. The antibody may bind a combined epitope on CD94 and NKG2A or and epitope on NKG2A alone. In another embodiment, the agent is an antibody that binds to HLA-E and inhibits the interaction between human HLA-E and human NKG2A proteins.

In one aspect the NKG2A neutralizing agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR, and a multispecific antibody.

Optionally, the anti-NKG2A antibodies do not demonstrate substantial specific binding to human Fcγ receptors, e.g. CD16. Optionally, the anti-NKG2A antibodies lack substantial specific binding or have low or decreased specific binding to one or more, or all of, human CD16, CD32A, CD32B or CD64. Exemplary antibodies may comprise constant regions of various heavy chains that are known not to bind or to have low binding to Fcγ receptors. One such example is a human IgG4 constant region. In one embodiment, the IgG4 antibody comprises a modification to prevent the formation of half antibodies (fab arm exchange) in vivo, e.g., the antibody comprises an IgG4 heavy chain comprising a serine to proline mutation in residue 241, corresponding to position 228 according to the EU-index (Kabat et al., "Sequences of proteins of immunological interest", 5$^{th}$ ed., NIH, Bethesda, M L, 1991). Such modified IgG4 antibodies will remain intact in vivo and maintain a bivalent (high affinity) binding to NKG2A, as opposed to native IgG4 that will undergo fab arm exchange in vivo such that they bind to NKG2A in monovalent manner which can alter binding affinity. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The present invention thus concerns antibodies or other agents binding to NKG2A. In one aspect, the antibody binds to NKG2A with a KD at least 100-fold lower than to human NKG2C and/or NKG2E.

In one aspect of the invention, the agent reduces CD94/NKG2A-mediated inhibition of a CD94/NKG2A-expressing lymphocyte by interfering with CD94/NKG2A signalling by, e.g., interfering with the binding of HLA-E by NKG2A, preventing or inducing conformational changes in the CD94/NKG2A receptor, and/or affecting dimerization and/or clustering of the CD94/NKG2A receptor.

In one aspect of the invention, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10,000 fold lower than to NKG2C. In another aspect of the invention, the agent binds to an extracellular portion of NKG2A with a KD at least 100 fold lower than to NKG2C, NKG2E and/or NKG2H molecules. In a further preferred aspect, the agent binds to an extracellular portion of NKG2A with a KD at least 150, 200, 300, 400, or 10,000 fold lower than to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporated herein by reference.

The anti-NKG2A antibody can be a humanized antibody, for example comprising a VH human acceptor framework from a human acceptor sequence selected from, e.g., VH1_18, VH5_a, VH5_51, VH1_f, and VH1_46, and a JH6 J-segment, or other human germline VH framework sequences known in the art. The VL region human acceptor sequence may be, e.g., VKI_O2/JK4.

In one embodiment, the antibody is a humanized antibody based on antibody Z270. Different humanized Z270 heavy chain variable regions are shown in SEQ ID NOS: 4-8, with optionally further comprising a C-terminal serine (S) residue. The HumZ270VH6 variable region of SEQ ID NO: 4 is based on a human VH5_51 gene; the HumZ270VH1 variable region of SEQ ID NO: 5 is based on a human VH1_18 gene; the humZ270VH5 variable region of SEQ ID NO: 6 is based on a human VH5_a gene; the humZ270VH7 variable region of SEQ ID NO: 7 is based on a human VH1_f gene; and the humZ270VH8 variable region of SEQ ID NO: 8 is based on a human VH1_46 gene; all with a human JH6 J-segment. Each of these antibodies retains high affinity binding to NKG2A, with low likelihood of a host immune response against the antibody as the 6 C-terminal amino acid residues of the Kabat H-CDR2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of SEQ ID NOS: 4-8, or an amino acid sequence at least 50%, 60%, 70%, 80%, 90%, 95%, 98% or 99% identical thereto, and (ii) a light chain variable region of SEQ ID NO: 9, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 10-14, or an amino acid sequence at least 50%, 60%, 70%, 80%, 90%, 95%, 98% or 99% identical thereto, and (ii) a light chain comprising the amino acid sequence of SEQ ID NO: 15, or an amino acid sequence at least 50%, 60%, 70%, 80%, 90%, 95%, 98% or 99% identical thereto.

The antibody having a heavy chain variable region of any of SEQ ID NOS: 4-8 and a light chain variable region of SEQ ID NO: 9 neutralizes the inhibitory activity of NKG2A, but does not substantially bind the activating receptors NKG2C, NKG2E or NKG2H. This antibody furthermore competes with HLA-E for binding to NKG2A on the surface of a cell. In one aspect, the agent comprises H-CDR1, H-CDR2 and/or H-CDR3 sequences derived from the heavy chain variable region having the amino acid sequence of any of SEQ ID NOS: 4-8. In one aspect of the invention, the agent comprises L-CDR1, L-CDR2 and/or L-CDR3 sequences derived from the light chain variable region having the amino acid sequence of SEQ ID NO: 9.

Heavy chain variable regions
VH6
(SEQ ID NO: 4)
EVQLVQSGAEVKKPGESLKISCKGSGYSFTSYWMNWVRQMPGKGLEWMGRIDPYD
SETHYSPSFQGQVTISADKSISTAYLQWSSLKASDTAMYYCARGGYDFDVGTLY
WFFDVWGQGTTVTVS VH1:
(SEQ ID NO: 5)
QVQLVQSGAEVKKPGASVKVSCKASGYTFTSYWMNWVRQAPGQGLEWMGRIDPYDSETHYA
QKLQGRVTMTTDTSTSTAYMELRSLRSDDTAVYYCARGGYDFDVGTLYWFFDVWGQGTTVTVS VH5:
(SEQ ID NO: 6)
EVQLVQSGAEVKKPGESLRISCKGSGYSFTSYWMNWVRQMPGKGLEWMGRIDPYD
SETHYSPSFQGHVTISADKSISTAYLQWSSLKASDTAMYYCARGGYDFDVGTLY
WFFDVWGQGTTVTVS VH7:
(SEQ ID NO: 7)
EVQLVQSGAEVKKPGATVKISCKVSGYTFTSYWMNWVQQAPGKGLEWMGRIDPYDSETHY
AEKFQGRVTITADTSTDTAYMELSSLRSEDTAVYYCATGGYDFDVGTLYWFFDVWGQGTTVTVS VH8:
(SEQ ID NO: 8)
QVQLVQSGAEVKKPGASVKVSCKASGYTFTSYWMNWVRQAPGQGLEWMGRIDPYDSETHY
AQKFQGRVTMTRDTSTSTVYMELSSLRSEDTAVYYCARGGYDFDVGTLYWFFDVWGQGTTVTVS Light chain variable region
(SEQ ID NO: 9)
DIQMTQSPSSLSASVGDRVTITCRASENIYSYLAWYQQKPGKAPKLLIYNAKTLAEGVPSRFSGS
GSGTDFTLTISSLQPEDFATYYCQHHYGTPRTFGGGTKVEIK Heavy Chains (variable region domain amino acids underlined)
VH6:
(SEQ ID NO: 10)
<u>EVQLVQSGAEVKKPGESLKISCKGSGYSFTSYWMNWVRQMPGKGLEWMGRIDPYD
SETHYSPSFQGQVTISADKSISTAYLQWSSLKASDTAMYYCARGGYDFDVGTLY
WFFDVWGQGTTVTVS</u>SASTKGPSVFPLAPCSRSTSESTAALGCLVKDYFPEPVTVSWNSGALTSGV
HTFPAVLQSSGLYSLSSVVTVPSSSLGTKTYTCNVDHKP
SNTKVDKRVESKYGPPCPPCPAPEFLGGPSVFLFPPKPKDTLMIS
RTPEVTCVVVDVSQEDPEVQFNWYVDGVEVHNAK
TKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPEN
NYKTTPPVLDSDGSFFLYSRLTVDKSRWQEGNVFSCSVMHEALHNHYTQKSLSLSLGK VH1:
(SEQ ID NO: 11)
<u>QVQLVQSGAEVKKPGASVKVSCKASGYTFTSYWMNWVRQAPGQGLEWMGRIDPYDSETHYA
QKLQGRVTMTTDTSTSTAYMELRSLRSDDTAVYYCARGGYDFDVGTLYWFFDVWGQGTTVTVS</u>
SASTKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKPKD
TLMISRTPEVTCVVVDVSQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKSLS
LSLGK VH5:
(SEQ ID NO: 12)
<u>EVQLVQSGAEVKKPGESLRISCKGSGYSFTSYWMNWVRQMPGKGLEWMGRIDPYD
SETHYSPSFQGHVTISADKSISTAYLQWSSLKASDTAMYYCARGGYDFDVGTLY
WFFDVWGQGTTVTVS</u>SASTKGPSVFPLAPCSRSTSESTAALGCLVKDYFPEPVTVSWNSGALTSGV
HTFPAVLQSSGLYSLSSVVTVPSSSLGTKTYTCNVDHKP
SNTKVDKRVESKYGPPCPPCPAPEFLGGPSVFLFPPKPKDTLMIS
RTPEVTCVVVDVSQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKSLS
LSLGK VH7:
(SEQ ID NO: 13)
<u>EVQLVQSGAEVKKPGATVKISCKVSGYTFTSYWMNWVQQAPGKGLEWMGRIDPYDSETHY
AEKFQGRVTITADTSTDTAYMELSSLRSEDTAVYYCATGGYDFDVGTLY
WFFDVWGQGTTVTVS</u>SASTKGPSVFPLAPCSRSTSESTAALGCLVKDYFPEPVTVSWNSGALTSGV
HTFPAVLQSSGLYSLSSVVTVPSSSLGTKTYTCNVDHKP
SNTKVDKRVESKYGPPCPPCPAPEFLGGPSVFLFPPKPKDTLMIS
RTPEVTCVVVDVSQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKSLS
LSLGK -continued

VH8:

(SEQ ID NO: 14)
QVQLVQSGAEVKKPGASVKVSCKASGYTFTSYWMNWVRQAPGQGLEWMGRIDPYDSETHY
AQKFQGRVTMTRDTSTSTVYMELSSLRSEDTAVYYCARGGYDFDVGTLYWFFDVWGQGTTVTVS
SASTKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPEN
NYKTTPPVLDSDGSFFLYSRLTVDKSRWQEGNVFSCSVMHEALHNHYTQKSLSLSLGK

Light chain (variable region domain amino acids underlined)

(SEQ ID NO: 15)
DIQMTQSPSSLSASVGDRVTITCRASENIYSYLAWYQQKPGKAPKLLIYNAKTLAEGVPSRFSGS
GSGTDFTLTISSLQPEDFATYYCQHHYGTPRTFGGGTKVEIKRTVAAPSVFIFPPSD-
EQLKSGTASVVC
LLNNFYPREAKVQWKVDNALQSGNSQESVTEQDSKDSTYSLSSTLTLSKADYEKHKVYACEVTHQG
LSSPVTKSFNRGEC

Monalizumab, CDRs on heavy and light chains
Heavy chain CDRs, according to Kabat numbering scheme:
H-CDR1:

(SEQ ID NO: 16)
SYWMN

H-CDR2:

(SEQ ID NO: 17)
RIDPYDSETHYAQKLQG

H-CDR3:

(SEQ ID NO: 18)
GGYDFDVGTLYWFFDV

Light chain CDRs according to Kabat numbering scheme:
L-CDR1:

(SEQ ID NO: 19)
RASENIYSYLA

L-CDR2:

(SEQ ID NO: 20)
NAKTLAE

L-CDR3:

(SEQ ID NO: 21)
QHHYGTPRT

In one aspect, the anti-NKG2A antibody is an antibody comprising a H-CDR1 corresponding to residues 31-35 of SEQ ID NOS: 4-8 (or of SEQ ID NOS: 10-14), a H-CDR2 corresponding to residues 50-60 (optionally 50-66 when including amino acids of human origin) of SEQ ID NOS: 4-8 (or of SEQ ID NOS: 10-14), and a H-CDR3 corresponding to residues 99-114 (95-102 according to Kabat) of SEQ ID NOS: 4-8 (or of SEQ ID NOS: 10-14). In one embodiment, the H-CDR2 corresponding to residues 50-66 of SEQ ID NOS: 4-8 (or of SEQ ID NOS: 10-14). Optionally, a CDR may comprise one, two, three, four, or more amino acid substitutions.

In one aspect, the anti-NKG2A antibody is an antibody comprising a L-CDR1 corresponding to residues 24-34 of SEQ ID NOS: 9 or 15, a L-CDR2 corresponding to residues 50-56 of SEQ ID NOS: 9 or 15, and an L-CDR3 corresponding to residues 89-97 of SEQ ID NOS: 9 or 15. Optionally, a CDR may comprise one, two, three, four, or more amino acid substitutions.

In one aspect, the anti-NKG2A antibody is an antibody comprising a H-CDR1 corresponding to residues 31-35 of SEQ ID NOS: 4-8, a H-CDR2 corresponding to residues 50-60 (optionally 50-66) of SEQ ID NOS: 4-8, and a H-CDR3 corresponding to residues 99-114 (95-102 according to Kabat) of SEQ ID NOS: 4-8, a L-CDR1 corresponding to residues 24-34 of SEQ ID NO: 9, a L-CDR2 corresponding to residues 50-56 of SEQ ID NO: 9, and an L-CDR3 corresponding to residues 89-97 of SEQ ID NO: 9.

In one aspect, the anti-NKG2A antibody is an antibody comprising the heavy chain H-CDR1, H-CDR2 and H-CDR3 domains having the amino acid sequences of SEQ ID NOS: 16-18, and the light chain L-CDR1, L-CDR2 and L-CDR3 domains having the amino acid sequences of SEQ ID NOS: 19-21, respectively.

In one aspect, the agent is monalizumab, an anti-NKG2A antibody having the heavy chain variable region amino acid sequence of SEQ ID NO: 5 and the light chain variable region amino acid sequence of SEQ ID NO: 9. In one aspect, the agent is monalizumab, an anti-NKG2A antibody having the heavy chain amino acid sequence of SEQ ID NO: 11 and the light chain amino acid sequence of SEQ ID NO: 15.

In one aspect, the agent comprises H-CDR1, H-CDR2 and/or H-CDR3 sequences derived from the VH having the amino acid sequence of SEQ ID NO: 22. In one aspect of the invention, the agent comprises L-CDR1, L-CDR2 and/or L-CDR3 sequences derived from the VL having the amino acid sequence of SEQ ID NO: 23. In one aspect, the agent comprises H-CDR1, H-CDR2 and/or H-CDR3 sequences derived from the VH having the amino acid sequence of SEQ ID NO: 22, and L-CDR1, L-CDR2 and/or L-CDR3 sequences derived from the VL having the amino acid sequence of SEQ ID NO: 23. The antibody having the heavy chain variable region of SEQ ID NO: 22 and a light chain variable region of SEQ ID NO: 23 neutralizes the inhibitory activity of NKG2A, and also binds the activating receptors NKG2C, NKG2E or NKG2H. This antibody does not compete with HLA-E for binding to NKG2A on the surface of a cell (i.e. it is a non-competitive antagonist of NKG2A).

(SEQ ID NO: 22)
EVQLVESGGGLVKPGGSLKLSCAASGFTFSSYAMSWVRQSPEKRLEWVA
EISSGGSYTYYPDTVTGRFTISRDNAKNTLYLEISSLRSEDTAMYYCTR
HGDYPRFFDVWGAGTTVTSS (SEQ ID NO: 23)
QIVLTQSPALMSASPGEKVTMTCSASSSVSYIYWYQQKPRSSPKPWIYL
TSNLASGVPARFSGSGSGTSYSLTISSMEAEDAATYYCQQWSGNPYTFG
GGTKLEIK

In one aspect, the agent comprises amino acid residues 31-35, 50-60, 62, 64, 66, and 99-108 of the variable-heavy (VH) domain (SEQ ID NO: 22 and amino acid residues 24-33, 49-55, and 88-96 of the variable-light (VL) domain (SEQ ID NO: 23), optionally with one, two, three, four, or more amino acid substitutions. In one aspect, the agent is a humanized antibody, for example an agent comprising heavy and light chain variable regions as disclosed in PCT publication no. WO2009/092805, the disclosure of which is incorporated herein by reference.

In one aspect, the agent is a fully human antibody which has been raised against the CD94/NKG2A epitope to which any of the aforementioned antibodies bind.

It will be appreciated that, while the aforementioned antibodies can be used, other antibodies can recognize and be raised against any part of the NKG2A polypeptide so long as the antibody causes the neutralization of the inhibitory activity of NKG2A. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Optionally, the epitope is the epitope specifically recognized by an antibody having a heavy chain variable region of SEQ ID NOS: 4-8 and a light chain variable region of SEQ ID NO: 9.

In one aspect, the agent competes with humZ270 antibody disclosed in U.S. Pat. No. 8,206,709 (the disclosure of which is incorporated herein by reference) in binding to the extracellular portion of human CD94/NKG2A receptor. Competitive binding can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g. after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporate herein by reference.

PD-1 Neutralizing Agents

As used herein, the terms "PD-1" refers to the protein Programmed Death 1 (PD-1) (also referred to as "Programmed Cell Death 1"), an inhibitory member of the CD28 family of receptors, that also includes CD28, CTLA-4, ICOS and BTLA. The complete human PD-1 sequence can be found under GenBank Accession No. U64863, shown as follows:

(SEQ ID NO: 2)
MQIPQAPWPVVWAVLQLGWRPGWELDSPDRPWNPPTFFPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQFQTLVVGVVGGLLGSLVLLVWVLAVICSRAA

RGTIGARRTGQPLKEDPSAVPVFSVDYGELDFQWREKTPEPPVPCVPEQ

TEYATIVFPSGMGTSSPARRGSADGPRSAQPLRPEDGHCSWPL.

"PD-1" also includes any variant, derivative, or isoform of the PD-1 gene or encoded protein. PD-1 is expressed on activated B cells, T cells, and myeloid cells (Okazaki et al. (2002) Curr. Opin. Immunol. 14: 391779-82; Bennett et al. (2003) J Immunol 170:711-8). The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members.

The complete human PD-L1 sequence can be found under UniProtKB/Swiss-Prot, identifier Q9NZQ7-1, shown as follows:

(SEQ ID NO: 3)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR LRKGRMMDVK KCGIQDTNSK

KQSDTHLEET.

PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well.

A PD-1 neutralizing agent is an agent that neutralizes PD-1 or reduces the inhibitory activity of human PD-1. In the context of the present invention, "reduces the inhibitory activity of human PD-1", "neutralizes PD-1" or "neutralizes the inhibitory activity of human PD-1" refers to a process in which PD-1 is inhibited in its signal transduction capacity resulting from the interaction of PD-1 with one or more of its binding partners, such as PD-L1 or PD-L2. An agent that neutralizes the inhibitory activity of PD-1 decreases, blocks, inhibits, abrogates or interferes with signal transduction resulting from the interaction of PD-1 with one or more of its binding partners, such as PD-L1, PD-L2. Such an agent can thereby reduce the negative co-stimulatory signal mediated by or through cell surface proteins expressed on T lymphocytes, so as to enhance T-cell effector functions such as proliferation, cytokine production and/or cytotoxicity. A PD-1 neutralizing agent can interact with PD-1 and/or with one or more of its binding partners, e.g. PD-L1 and PD-L2.

In some embodiments, the PD-1 neutralizing agent is an anti-PD-L1 monoclonal antibody that inhibits the binding of PD-L1 to PD-1. In some embodiments, the PD-1 neutralizing agent is an anti-PD-1 monoclonal antibody that inhibits the binding of PD-1 to PD-L1. In some embodiments, the PD-1 neutralizing agent is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the PD-1 neutralizing agent is an anti-PD-L1 antibody. In some embodiments, the PD-1 neutralizing agent is selected from the group consisting of antibodies YW243.55.570, MPDL3280A (atezolizumab, Tecentriq®), MDX-1105, and durvalumab (MEDI4736, Imfinzi®). MDX-1105, also known as BMS-936559, is an anti-PD-L1 antibody described in WO2007/005874. Antibody YW243.55.570 is an anti-PD-L1 described in WO 2010/077634. Examples of anti-PD-L1 antibodies useful for the methods of this invention, and methods for making thereof are also described in WO 2010/077634 A1 and U.S. Pat. No. 8,217,149, which are incorporated herein by reference.

In some embodiments, the PD-1 neutralizing agent is a PD-L1 antibody that is durvalumab. Durvalumab (MEDI4736, Imfinzi™) is a human monoclonal antibody directed against human PD-L1 that is capable of blocking the binding of PD-L1 to both the PD-1 and CD80 receptors. Disclosure related to durvalumab can be found in U.S. Pat. Nos. 8,779,108 and 9,493,565, which are incorporated herein by reference. Durvalumab has the heavy and light chains of amino acid sequences SEQ ID NO: 26 and SEQ ID NO: 27, respectively. The heavy chain variable region of durvalumab is shown in SEQ ID NO: 24 and the light chain variable region of durvalumab is shown in SEQ ID NO: 25.

In another embodiment, the PD-1 neutralizing agent is an anti-PD-L1 antibody (or an antigen-binding portion thereof) competing with durvalumab for binding to PD-L1. In some embodiments, the anti-PD-L1 antibody binds to the same epitope as durvalumab. In certain embodiments, the anti-PD-L1 antibody has the same heavy and light chain CDRs as durvalumab.

In one aspect, the PD-1 neutralizing agent (e.g. an agent derived from durvalumab) comprises (i) the heavy chain variable region of SEQ ID NO: 24, or an amino acid sequence at least 50%, 60%, 70%, 80%, 90%, 95%, 98% or 99% identical thereto, and (ii) the light chain variable region of SEQ ID NO: 25, or an amino acid sequence at least 50%, 60%, 70%, 80%, 90%, 95%, 98% or 99% identical thereto. In one aspect, the PD-1 neutralizing agent (e.g. an agent derived from durvalumab) comprises (i) the heavy chain of SEQ ID NO: 26, or an amino acid sequence at least 50%, 60%, 70%, 80%, 90%, 95%, 98% or 99% identical thereto, and (ii) the light chain of SEQ ID NO: 27, or an amino acid sequence at least 50%, 60%, 70%, 80%, 90%, 95%, 98% or 99% identical thereto. In one aspect, the PD-1 neutralizing agent comprises H-CDR1, H-CDR2 and/or H-CDR3 sequences derived from the heavy chain variable region comprising the amino acid sequence of SEQ ID NO: 24. In one aspect, the PD-1 neutralizing agent comprises L-CDR1, L-CDR2 and/or L-CDR3 sequences derived from the light chain variable region comprising the amino acid sequence of SEQ ID NO: 25. Optionally, CDRs are determined according to Kabat.

In one aspect, the PD-1 neutralizing agent comprises the heavy chain H-CDR1, H-CDR2 and H-CDR3 domains having the amino acid sequences of SEQ ID NOS: 28-30, respectively, and the light chain L-CDR1, L-CDR2, L-CDR3 domains having the amino acid sequences of SEQ ID NOS: 31-33, respectively.

Heavy Chain Variable Region of Durvalumab:

```
                                              (SEQ ID NO: 24)
EVQLVESGGGLVQPGGSLRLSCAASGFTFSRYWMSWVRQAPGKGLEWVA

NIKQDGSEKYYVDSVKGRFTISRDNAKNSLYLQMNSLRAEDTAVYYCAR

EGGWFGELAFDYWGQGTLVTVSS
```

Light Chain Variable Region of Durvalumab

```
                                              (SEQ ID NO: 25)
EIVLTQSPGTLSLSPGERATLSCRASQRVSSSYLAWYQQKPGQAPRLLI

YDASSRATGIPDRESGSGSGTDFTLTISRLEPEDFAVYYCQQYGSLPWT

FGQGTKVEIK
```

Heavy Chain of Durvalumab (Variable Region Underlined)

```
                                              (SEQ ID NO: 26)
EVQLVESGGGLVQPGGSLRLSCAASGFTFSRYWMSWVRQAPGKGLEWVA

NIKQDGSEKYYVDSVKGRFTISRDNAKNSLYLQMNSLRAEDTAVYYCAR

EGGWFGELAFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKRVEPKSCDKTHTCPPCPAPEFEGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPASIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPGK
```

Light Chain of Durvalumab (Variable Region Underlined)

```
                                              (SEQ ID NO: 27)
EIVLTQSPGTLSLSPGERATLSCRASQRVSSSYLAWYQQKPGQAPRLLI

YDASSRATGIPDRESGSGSGTDFTLTISRLEPEDFAVYYCQQYGSLPWT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSENRGEC
```

Durvalumab, Heavy Chain CDRs:

```
H-CDR1:
                                (SEQ ID NO: 28)
GFTFSRYWMS

H-CDR2:
                                (SEQ ID NO: 29)
NIKQDGSEKYYVDSVKG

H-CDR3:
                                SEQ ID NO: 30)
EGGWFGELAFDY
```

Durvalumab, Light Chain CDRs:

```
L-CDR1:
                                (SEQ ID NO: 31)
RASQRVSSSYLA

L-CDR2:
                                (SEQ ID NO: 32)
DASSRAT

L-CDR3:
                                (SEQ ID NO: 33)
QQYGSLPWT
```

In another embodiment, the PD-1 neutralizing agent is an anti-PD-L1 antibody that is atezolizumab (MPDL3280A, Tecentriq®, CAS Registry Number: 1422185-06-5). Optionally, the anti-PD-L1 antibody comprises a heavy chain variable region comprising the amino acid sequence:

```
                                (SEQ ID NO: 34)
EVQLVESGGGLVQPGGSLRLSCAASGFTFSDSWIHWVRQAPGKGLEWVA
WISPYGGSTYYADSVKGRFTISADTSKNTAYLQMNSLRAEDTAVYYCAR
RHWPGGFDYWGQGTLVTVSS
or
                                (SEQ ID NO: 35)
EVQLVESGGGLVQPGGSLRLSCAASGFTFSDSWIHWVRQAPGKGLEWVA
WISPYGGSTYYADSVKGRFTISADTSKNTAYLQMNSLRAEDTAVYYCAR
RHWPGGFDYWGQGTLVTVSSASTK
``` and a light chain variable region comprising the amino acid sequence:

```
                                (SEQ ID NO: 36)
DIQMTQSPSSLSASVGDRVTITCRASQDVSTAVAWYQQKPGKAPKLLIY

SASFLYSGVPSRESGSGSGTDFTLTISSLQPEDFATYYCQQYLYHPATF

GQGTKVEIKR.
```

In one aspect, the PD-1 neutralizing agent comprises (i) a heavy chain or heavy chain variable region of SEQ ID NO: 37, or an amino acid sequence at least 50%, 60%, 70%, 80%, 90%, 95%, 98% or 99% identical thereto, and (ii) a light chain or light chain variable region of SEQ ID NO: 38, or an amino acid sequence at least 50%, 60%, 70%, 80%, 90%, 95%, 98% or 99% identical thereto.

```
                                (SEQ ID NO: 37)
EVQLVESGGGLVQPGGSLRLSCAASGFTFSDSWIHWVRQAPGKGLEWVA
WISPYGGSTYYADSVKGRFTISADTSKNTAYLQMNSLRAEDTAVYYCAR
RHWPGGFDYWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
```

```
-continued
EQYASTYRVVSVLTVLHQDWLNGKEYKCKVSNKALPAPIEKTISKAKGQ
PREPQVYTLPPSREEMTKQVSLTCLVKGFYPSDIAVEWESNGQPENYKT
TPPVLDSDGSFFLYSKLTVDKSRWQQGNVFSCSVMHEALHNHYTQKSLS
LSPG
```

```
                                (SEQ ID NO: 38)
DIQMTQSPSSLSASVGDRVTITCRASQDVSTAVAWYQQKPGKAPKLLIY
SASFLYSGVPSRESGSGSGTDFTLTISSLQPEDFATYYCQQYLYHPATF
GQGTKVEIKRTVAAPSVFIFPPSDEQLKSGTASVVCLLNFYPREAKVQW
KVDNALQSGNSQESVTEQDSKDSTYSLSSTLTLSKADYEKHKVYACEVT
HQGLSSPVTKSENRGEC
```

In some embodiments, the PD-1 neutralizing agent is an anti-PD-1 antibody that inhibits the binding of PD-1 to PD-L1. In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9): 846-56). In another embodiment, the anti-PD-1 antibody or fragment thereof competes with nivolumab for binding to PD-1. In some embodiments, the anti-PD-1 antibody binds to the same epitope as nivolumab. In certain embodiments, the anti-PD-1 antibody has the same heavy and light chain CDRs as nivolumab.

In another embodiment, the anti-PD-1 antibody is pembrolizumab. Pembrolizumab (also known as "KEYTRUIDA®", lambrolizumab, and MK-3475) is a humanized monoclonal IgG4 antibody directed against human cell surface receptor PD-1. Pembrolizumab is described, for example, in U.S. Pat. No. 8,900,587). Pembrolizumab has been approved by the FDA for the treatment of relapsed or refractory melanoma and advanced NSCLC. In another embodiment, the anti-PD-1 antibody (or an antigen-binding portion thereof) competes with pembrolizumab for binding to PD-1. In some embodiments, the anti-PD-1 antibody binds to the same epitope as pembrolizumab. In certain embodiments, the anti-PD-1 antibody has the same heavy and light chain CDRs as pembrolizumab.

A NKG2A neutralizing agent or aPD-1 neutralizing agent such as an antibody can be incorporated in a pharmaceutical formulation in a concentration from 1 mg/ml to 500 mg/ml, wherein said formulation has a pH from 2.0 to 10.0. The NKG2A neutralizing agent and the PD-1 neutralizing agent can be comprised in the same or separate pharmaceutical formulations. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: *The Science and Practice of Pharmacy,* 19$^{th}$ edition, 1995.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Administration of pharmaceutical compositions according to the invention may be through several routes of administration, for example, intravenous. Suitable antibody formulations can also be determined by examining experiences with other already developed therapeutic monoclonal antibodies.

Also provided are kits, for example kits which include:
(i) a pharmaceutical composition containing a NKG2A neutralizing agent such as an anti-NKG2A antibody, and a PD-1 neutralizing agent such as an anti-PD-1 antibody or an anti-PD-L1 antibody, or
(ii) a first pharmaceutical composition containing a PD-1 neutralizing agent such as an anti-PD-1 antibody or an anti-PD-L1 antibody, and a second pharmaceutical composition containing a NKG2A neutralizing agent such as an anti-NKG2A antibody, or
(iii) a pharmaceutical composition containing a NKG2A neutralizing agent such as an anti-NKG2A antibody, and instructions to administer said NKG2A neutralizing agent with a PD-1 neutralizing agent such as an anti-PD-1 antibody or an anti-PD-L1 antibody, or
(iv) a pharmaceutical composition containing a PD-1 neutralizing agent such as an anti-PD-1 antibody or an anti-PD-L1 antibody, and instructions to administer said PD-1 neutralizing agent with a NKG2A neutralizing agent such as an anti-NKG2A antibody.

A pharmaceutical composition may optionally be specified as comprising a pharmaceutically-acceptable carrier. A NKG2A or PD-1 neutralizing agent may optionally be specified as being present in a therapeutically effective amount adapted for use in any of the methods herein. The kits optionally also can include instructions, e.g., comprising administration schedules, to allow a practitioner (e.g., a physician, nurse, or patient) to administer the composition contained therein to a patient having cancer (e.g., a solid tumor, in particular a tumor that is not DNA mismatch-repair defective and/or that does not have microsatellite instability detected in two or more microsatellite makers). In any embodiment, a kit optionally can include instructions to administer said NKG2A neutralizing agent simultaneously, separately, or sequentially with said PD-1 neutralizing agent. The kit also can include a syringe.

Optionally, the kits include multiple packages of the single-dose pharmaceutical compositions each containing an effective amount of the NKG2A neutralizing agent, and/or the PD-1 neutralizing agent such as an anti-PD-1 or PD-L1 antibody, for a single administration in accordance with the methods provided above. Instruments or devices necessary for administering the pharmaceutical composition(s) also may be included in the kits. For instance, a kit may provide one or more pre-filled syringes containing an amount of the anti-NKG2A, anti-PD-1 or anti-PD-L1 antibody.

In one embodiment, the present invention provides a kit for treating a cancer or a tumor in a human patient, wherein said cancer or tumor is not MSI-H and/or not DNA mismatch repair defective, the kit comprising:
(a) a dose of an anti-NKG2A antibody comprising the H-CDR1, H-CDR2 and H-CDR3 domains of a heavy chain variable region having the sequence set forth in any of SEQ ID NOS: 4-8, and the L-CDR1, L-CDR2 and L-CDR3 domains of a light chain variable region having the sequence set forth in SEQ ID NO: 9; and/or
(b) a dose of an anti-PD-1 antibody or an anti-PD-L1 antibody, optionally a dose of durvalumab, optionally a dose of an anti-PD-L1 antibody comprising the heavy and light chain H-CDR1, H-CDR2 and H-CDR3 domains of durvalumab, optionally the H-CDR1, H-CDR2 and H-CDR3 domains of a heavy chain variable region having the sequence set forth in SEQ ID NO: 24, and the L-CDR1, L-CDR2 and L-CDR3 domains of a light chain variable region having the sequence set forth in SEQ ID NO: 25; and
(c) optionally, instructions for using said anti-NKG2A antibody and/or said anti-PD-1 or PD-L1 antibody in any of the methods described herein.

In one embodiment, the present invention provides a kit for treating a cancer or a tumor in a human patient, wherein said cancer or tumor is not MSI-H and/or not DNA mismatch repair defective, the kit comprising:
(a) a dose of an anti-NKG2A antibody comprising the heavy chain H-CDR1, H-CDR2 and H-CDR3 domains having the sequences of SEQ ID NOS: 16-18, and the light chain L-CDR1, L-CDR2 and L-CDR3 domains having the sequences of SEQ ID NOS: 19-21, respectively; and/or
(b) a dose of an anti-PD-L1 antibody comprising the heavy chain H-CDR1, H-CDR2 and H-CDR3 domains having the amino acid sequences of SEQ ID NOS: 28-30, and the light chain L-CDR1, L-CDR2 and L-CDR3 domains having the amino acid sequences of SEQ ID NOS: 31-33, respectively; and
(c) optionally, instructions for using said anti-NKG2A antibody and/or said anti-PD-1 or PD-L1 antibody in any of the methods described herein.

Diagnostics, Prognostics, and Treatment of Malignancies

Described are methods useful in the diagnosis, prognosis, monitoring and treatment of a cancer, particularly colorectal cancer, optionally advanced recurrent or metastatic colorectal cancer, characterized by tumors that are not DNA mismatch repair defective and/or that are microsatellite stable. Colorectal cancer (CRC) as used herein refers to colon cancer, rectal cancer, and colorectal cancer (cancer of both the colon and rectal areas).

Microsatellites are repeated sequences of DNA distributed throughout the genome. Although the length of these microsatellites is highly variable from person to person, each individual has microsatellites of a set length. These repeated sequences are common, and normal. The most common microsatellite in humans is a dinucleotide repeat of CA, which occurs tens of thousands of times across the genome. In cells with mutations in DNA repair genes, however, some of these sequences accumulate errors and become longer or shorter. The appearance of abnormally long or short microsatellites in an individual's DNA is referred to as microsatellite instability (MSI). Microsatellite instability is the condition of genetic hypermutability that results from impaired DNA mismatch repair (MMR). The presence of microsatellite instability (MSI) represents phenotypic evidence that MMR is not functioning normally. The absence of microsatellite instability is termed microsatellite stability (MSS).

MSI is a key factor in several cancers including colorectal, endometrial, ovarian and gastric cancers (Soreide et al. (2006) The British Journal of Surgery 93:395-406; Ali-Fehmi et al. (2006) International Journal of Gynecological Pathology 25:223-229; Vauhkonen et al. (2006) Clinical Gastroenterology 20:651-674).

Colorectal cancer studies have demonstrated two mechanisms for MSI occurrence. The first is in hereditary non-polyposis colorectal cancer (HNPCC) or Lynch Syndrome, where an inherited mutation in a DNA mismatch-repair gene causes a microsatellite repeat replication error to go unfixed. The replication error results in a frameshift mutation that inactivates or alters major tumor suppressor genes and, ultimately, the prevention of cancer. The second mechanism whereby MSI causes colorectal cancer is an epigenetic change which silences an essential DNA mismatch-repair gene. In both cases, microsatellite insertions and deletions within tumor suppressor gene coding regions result in uncontrolled cell division and tumor growth.

Five markers have been recommended by the National Cancer Institute to screen for MSI in HNPCC tumors (often called "Bethesda markers"). These five markers of MSI presence are: two mononucleotide repeats BAT25 and BAT26, and three dinucleotide repeats D5S346, D2S123, and D17S250 (Umar et al (2004) Journal of the National Cancer Institute 96:261-268). Generally, MSI detection in two of the five "Bethesda markers" is considered a positive result or high probability of MSI (MSI-High or MSI-H). Standard methods for detecting MSI in biological samples include the use of Promega's microsatellite instability assay (MSI Analysis System) that includes five mononucleotide markers chosen for their sensitivity and specificity, these five markers are: BAT-25, BAT-26, NR-21, NR-24 and MONO27 (Bacher et al. (2004) Disease Markers 20:237-250).

In most cases, the genetic basis for instability in MSI tumors is an inherited germline alteration in any one or more of the five human MMR genes: MSH2, MLH1, MSH6, PMS2, and PMS1.

Another MSI, called elevated microsatellite alterations at selected tetranucleotide repeats (EMAST), was recently discovered. However, EMAST is unique in that it is not derived from MMR, and it is commonly associated with TP53 mutations (Boland et al. (2010) Gastroenterology 138 (6): 2073-2087).

Thus, microsatellite instability in a tumor can be determined by assessing microsatellite markers and/or MMR genes.

In certain embodiments, the individual who is treated with the combination of NKG2A-neutralizing agent and PD-1 neutralizing agent has no instability (MSS) and has no alteration (e.g. mutation, deficiency in expression) in any of the MSH2, MLH1, MSH6 and PMS2 gene or protein (optionally further PMS1).

In some embodiments, the invention includes a method of treating a tumor in an individual, e.g., colorectal tumor, comprising (i) identifying an individual who has a tumor that is not DNA mismatch repair defective, and (ii) administering to the individual an effective amount of a NKG2A-neutralizing agent and an effective amount of a PD-1 neutralizing agent. Optionally, the individual has a tumor that has no microsatellite instability (is MSS stable) and has no alternation in any of MSH2, MLH1, MSH6 and PMS2 genes or proteins.

The DNA mismatch repair status of a tumor, optionally the MMR status and/or microsatellite status in an individual can be measured prior to administering any composition or utilizing any method disclosed herein.

A biological sample from an individual, for example from a biopsy, can be obtained and assessed. MMR status and/or microsatellite status can be determined by any methods known in the art, see, e.g., Umar et al. Journal of the National Cancer Institute 2004; 96(4):261-268 and Bacher et al. Disease Markers 2004; 20:237-250. In one embodiment, MMR status is assessed by immunohistochemical analysis demonstrating the presence or absence of expression of any one or more of the following proteins: MLH1, MSH2, MSH6, or PMS2. In one embodiment, microsatellite status is assessed by detecting high-frequency microsatellite instability in microsatellite markers, for example BAT-25, BAT-26, NR-21, NR-24, MONO27, D5S346, D2S123, and D17S250. In one embodiment, microsatellite instability detected for two or more microsatellite markers, for example for BAT-25, BAT-26, NR-21, NR-24, and/or MONO27, indicates a MSI-H status, while microsatellite instability for a single MSI marker or no instability for any of the MSI markers tested is interpreted as microsatellite instability-Low (MSI-L) and microsatellite stable (MSS), respectively.

In one embodiment, a tumor that is not DNA mismatch repair defective or that is MSS has no microsatellite instability or microsatellite instability detected at less than two or more microsatellite markers, for example BAT-25, BAT-26, NR-21, NR-24, or MONO27, and no absence of protein expression at any one or more of proteins MLH1, MSH2, MSH6, or PMS2.

In some embodiments, the invention includes a method of treating a tumor in an individual, e.g., colorectal tumor, comprising (i) identifying an individual who has a MSS tumor and (ii) administering to the individual an effective amount of a NKG2A-neutralizing agent, optionally further administering to the individual an effective amount of a PD-1 neutralizing agent. In some embodiments, the invention provides a method of treating a tumor, e.g., a colorectal tumor, comprising (i) identifying an individual who has a tumor that is not a MSI-High (MSI-H) tumor (e.g. a MSS or a MSI-Low tumor) and (ii) administering to the individual an effective amount of a NKG2A-neutralizing agent, optionally further administering to the individual an effective amount of a PD-1 neutralizing agent.

In one embodiment, MSI-H tumors have greater than at least about 30% of unstable MSI markers. In one embodiment, MSI-L tumors do have unstable MSI markers but less than about 10%, less than about 20%, or less than about 30% of the MSI markers of said tumors are unstable MSI markers. In one embodiment, MSS tumors have no unstable MSI marker. In some embodiments, a colorectal cancer is MSI-L when less than about 30%, less than about 20% or less than about 10% of the tested MSI markers exhibit instability. In some embodiments, a colorectal cancer is MSS when none of the tested MSI markers exhibit instability.

In certain embodiments, the present invention is directed to a method of treating a cancer that is MSI-L or MSS.

In certain embodiments, the present invention is directed to a method of treating a cancer comprising 1) identifying the microsatellite status of a tumor and 2) administering a therapy (e.g. a NKG2A-neutralizing agent and a PD-1-neutralizing agent) to the subject based on the microsatellite status. In other embodiments, the subject has MSI-L. In embodiments, the patient is MSI stable.

When treating an individual having a non-DNA mismatch repair defective tumor, a compound (e.g. antibody) that neutralizes the inhibitory activity of a human NKG2A polypeptide can advantageously be administered according to a treatment regimen described herein, optionally to an individual having a cancer who has received, or who is undergoing, surgery to remove cancer cells. A neutralizing anti-NKG2A antibody, optionally in the absence or optionally in combination with a PD-1-neutralizing agent, e.g. a neutralizing anti-PD-1 or anti-PD-L1 antibody, to treat subjects afflicted with cancer, particularly CRC and mCRC. In one embodiment, the invention provides an anti-NKG2A antibody, and optionally further an anti-PD-1 antibody in combination, to treat subjects having a solid tumor (e.g., a solid tumor, an advanced refractory solid tumor). In a particular embodiment, the anti-NKG2A antibody comprises a heavy chain variable region of any of SEQ ID NOS: 4-8 and a light chain variable region of SEQ ID NO: 9. In one embodiment, the antibody that neutralizes the inhibitory activity of PD-1 is selected from the group consisting of pembrolizumab, nivolumab, durvalumab and MPDL3280A, in particular durvalumab.

As used herein, adjunctive or combined administration (co-administration) includes simultaneous administration of the compounds in the same or different dosage form, or separate administration of the compounds (e.g., sequential administration). Thus, a NKG2A-neutralizing agent can be used in combination with a PD-1-neutralizing agent. For example, an anti-NKG2A antibody and an anti-PD-1 or anti-PD-L1 antibody can be simultaneously administered in a single formulation. Alternatively, the NKG2A-neutralizing agent and the PD-1-neutralizing agent can be formulated for separate administration and are administered concurrently or sequentially.

Optionally, an individual may have a cancer that is resistant, has not responded, has relapsed and/or progressed despite (e.g. during or following) surgery and/or treatment with a therapeutic agent, e.g. a chemotherapeutic agent or radiotherapy. In any embodiment herein, treatment response can be defined and/or assessed according to well-known criteria, e.g. Response Evaluation Criteria In Solid Tumors (RECIST), such as version 1.1, see Eisenhauer et al. (2009) Eur. J. Cancer 45:228-247, or Immune-Related Response Criteria (irRC), see Wolchock et al. (2009) Clinical Cancer Research 15:7412-7420.

In another embodiment, the disclosure provides a method for the treatment or prevention of a CRC in an individual having a tumor that is not DNA mismatch repair defective, the method comprising:
a) identifying an individual who has a tumor that is not DNA mismatch-repair defective, optionally obtaining a biological sample comprising tumor cells from the individual and determining whether the tumor is DNA mismatch-repair defective,
b) detecting cells (e.g. tumor cells, tumor infiltrating immune cells, tumor infiltrating macrophages) that express PD-L1 in a sample from the individual, and
c) upon a determination that cells which express PD-L1 are comprised in the sample, administering to the individual an agent that neutralizes the inhibitory activity of NKG2A in combination with an agent that neutralizes the inhibitory activity of PD-1. The PD-L1 reference level can be characterized by any suitable conventionally used reference level. For example, if 1% or more, optionally 5% or more, optionally 10% or more, optionally 50% or more of tumor cells or cells from a tumor tissue sample express PD-L1 (e.g. using an immunohistochemistry-based assay). Example of such assays include the PD-L1 IHC 22C3 assay from pharmDx from Dako Denmark A/S. In this assay, PD-L1 expression level is measured using the tumor proportion score (TPS), the percentage of tumor cells staining for PD-L1 (0% to 100%). Optionally, a reference level is a level for a non-high PD-L1 expression, optionally wherein less 50% tumor cells express PD-L1 (e.g., the patients have a TPS of less than 50%).

The treatment regimens and methods described herein may be used with or without a prior step of detecting the expression HLA-E on cells in a biological sample obtained from an individual (e.g. a biological sample comprising cancer cells, cancer tissue or cancer-adjacent tissue). In one embodiment, the cancer treated with the methods disclosed herein is a cancer characterized by high levels of HLA-E. However, it will be appreciated that a patient having a cancer can be treated with the NKG2A neutralizing agent with or without a prior detection step to assess expression of HLA-E on the surface of tumor cells. Advantageously, the treatment methods can comprises a step of detecting a HLA-E nucleic acid or polypeptide in a biological sample of a tumor (e.g. on a tumor cell) from an individual. A determination that a biological sample expresses HLA-E (e.g. prominently expresses; expresses HLA-E at a high level, high intensity of staining with an anti-HLA-E antibody, compared to a reference) indicates that the individual has a cancer that may have a strong benefit from treatment with an agent that inhibits NKG2A. In one embodiment, the method comprises determining the level of expression of a HLA-E nucleic acid or polypeptide in a biological sample and comparing the level to a reference level (e.g. a value, weak cell surface staining, etc.) corresponding to a healthy individual. A determination that a biological sample expresses an HLA-E nucleic acid or polypeptide at a level that is increased compared to the reference level may indicate that the individual has a cancer that can be treated with an agent that inhibits NKG2A.

Determining whether an individual has cancer cells that express an HLA-E polypeptide can for example comprise obtaining a biological sample (e.g. by performing a biopsy) from the individual that comprises cancer cells, bringing said cells into contact with an antibody that binds an HLA-E polypeptide, and detecting whether the cells express HLA-E on their surface. Optionally, determining whether an individual has cancer cells that express HLA-E comprises conducting an immunohistochemistry assay. Optionally determining whether an individual has cancer cells that express HLA-E comprises conducting a flow cytometry assay.

In the treatment methods, when NKG2A-neutralizing agent is administered in combination with an anti-PD-1 or anti-PD-L1 antibody, the NKG2A-neutralizing agent and anti-PD-1 or anti-PD-L1 antibody can be administered separately, together or sequentially, or in a cocktail. In some embodiments, the NKG2A-neutralizing agent is administered prior to the administration of the anti-PD-1 or anti-PD-L1 antibodies. For example, the NKG2A-neutralizing agent can be administered approximately 0 to 30 days prior to the administration of the anti-PD-1 or anti-PD-L1 antibodies. In some embodiments, antibody NKG2A-neutralizing agent is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the anti-PD-1 or anti-PD-L1 antibodies. In some embodiments, a NKG2A-neutralizing agent is administered concurrently with the administration of the anti-PD-1 or anti-PD-L1 antibodies. In some embodiments, a NKG2A-neutralizing agent is administered after the administration of the anti-PD-1 or anti-PD-L1 antibodies. For example, a NKG2A-neutralizing agent can be administered approximately 0 to 30 days after the administration of the anti-PD-1 or anti-PD-L1 antibodies. In some embodiments, a NKG2A-neutralizing agent is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the anti-PD-1 or anti-PD-L1 antibodies.

Exemplary treatment protocols for treating a human with an anti-NKG2A antibody include, for example, administering to the patient an effective amount of an antibody that inhibits NKG2A, wherein the method comprises at least one administration cycle in which at least one dose of the anti-NKG2A antibody is administered at a dose of 1-10 mg/kg body weight. In one embodiment, the administration cycle is between 2 weeks and 8 weeks.

Exemplary treatment protocols for treating a human with an anti-NKG2A antibody include, for example, administering to the patient an effective amount of each of an antibody that inhibits NKG2A and an antibody that neutralizes the inhibitory activity of human PD-1, wherein the method comprises at least one administration cycle in which at least one dose of the anti-NKG2A antibody is administered at a dose of 0.1-10 mg/kg body or 1-10 mg/kg body weight and at least one dose of the anti-PD-1 or anti-PD-L1 antibody is administered at a dose of 1-20 mg/kg body weight. In one embodiment, the administration cycle is between 2 weeks and 8 weeks.

In one embodiment, the method comprises at least one administration cycle, wherein the cycle is a period of eight weeks or less, wherein for each of the at least one cycles, two, three or four doses of the anti-NKG2A antibody are administered at a dose of 1-10 mg/kg body weight. In one embodiment, each cycle further comprises the administration of two, three or four doses of the anti-PD-1 or anti-PD-L1 antibody at a dose of 1-20 mg/kg body weight.

The anti-NKG2A antibody can advantageously be administered in an amount that achieves a concentration in circulation that is at least 10, 20, or 30 times higher than the concentration required for substantially full (e.g., 90%, 95%) receptor saturation (e.g., as assessed by titrating anti-NKG2A antibody on NKG2A-expressing cells, for example in PBMC), or optionally in an amount that achieves a concentration in a extravascular tissue (e.g. the tumor tissue or environment) that is at least 10, 20, or 30 times higher than the concentration required for substantially full receptor saturation (e.g., as assessed by titrating anti-NKG2A antibody on NKG2A-expressing cells, for example in PBMC).

NKG2A+ NK cell response can be assessed using a suitable assay of cytotoxic activity of NKG2A-expressing NK cells toward HLA-E expressing target cells. Examples include assays based on markers of NK cell activation, for example CD107 or CD137 expression. Advantageously an amount of anti-NKG2A antibody can be administered so at to achieve and/or maintain a continuous (minimum) tissue concentration of at least 10 µg/ml. For example, the blood concentration to be achieved and/or maintained in order to achieve/maintain 10 µg/ml in a tissue can be between 100-110 µg/ml, 100-120 µg/ml, 100-130 µg/ml, 100-140 µg/ml, 100-150 µg/ml, 100-200 µg/ml, 100-250 µg/ml or 100-300 µg/ml.

Exemplary treatment protocols for an anti-NKG2A antibody such as humZ270 (monalizumab) used in the Examples herein having an $EC_{100}$ for NKG2A+ NK cell response of about 10 µg/ml comprise at least one administration cycle in which at least one dose of the anti-NKG2A antibody is administered at a dose of about 10 mg/kg, optionally 2-10 mg/kg, optionally 4-10 mg/kg, optionally 6-10 mg/kg, optionally 2-6 mg/kg, optionally 2-8 mg/kg, or optionally 2-4 mg/kg body weight. Optionally, at least 2, 3, 4, 5, 6, 7 or 8 doses of the anti-NKG2A antibody are administered. In one embodiment, the administration cycle is between 2 weeks and 8 weeks. In one embodiment, the administration cycle is 8 weeks. In one embodiment, the administration cycle is 8 weeks and comprises administering one dose of the anti-NKG2A antibody every two weeks (i.e. a total of four doses).

In one aspect of any of the embodiments herein, the anti-NKG2A antibody is administered once about every two weeks.

Exemplary treatment protocols for use with an anti-NKG2A antibody include for example, administering to the patient an anti-NKG2A antibody two times per month in an amount effective to maintain a continuous blood concentration of anti-NKG2A antibody of at least 40 µg/ml between at least two successive administrations of the anti-NKG2A antibody is between 2-10 mg/kg, optionally 2-6 mg/kg, optionally 2-4 mg/kg, optionally about 4 mg/kg body weight. These doses can optionally be administered so as to provide for continued blood concentration of anti-NKG2A antibody of at least 40 µg/ml throughout the treatment cycle. Achieving blood concentration of anti-NKG2A antibody of 40 µg/ml is expected to provide a tissue (e.g., extravascular tissue, tumor environment) concentration of about 4 µg/ml, in turn corresponding to the $EC_{50}$ for an antibody such as humanized Z270 (monalizumab).

Exemplary treatment protocols for use with an anti-NKG2A antibody include for example, administering to the patient an effective amount of an anti-NKG2A antibody, wherein the antibody is administered 2 times per month and the amount effective to maintain a continuous blood concentration of anti-NKG2A antibody of at least 100 µg/ml between at least two successive administrations of the anti-NKG2A antibody is between 4-10 mg/kg, optionally 4-6 mg/kg, optionally 4-8 mg/kg, optionally about 4 mg/kg, optionally about 6 mg/kg, optionally about 8 mg/kg, or optionally about 10 mg/kg. These doses can optionally be administered so as to provide for continued blood concentration of anti-NKG2A antibody of at least 100 μg/ml throughout the treatment cycle. Achieving blood concentration of anti-NKG2A antibody of 100 μg/ml is expected to provide a tissue (e.g., extravascular, tumor environment) concentration of about 10 μg/ml, in turn corresponding to the $EC_{100}$ for an antibody such as humanized Z270.

In certain embodiments, a dose (e.g. each dose) of the anti-NKG2A antibody (e.g. monalizumab) is administered at 0.1, 0.3, 1, 3, 4, 6, 8 or 10 mg/kg. In certain embodiments, a dose (e.g. each dose) of the anti-NKG2A antibody (e.g. monalizumab) is administered at a fixed dose of 7.5 mg, 22.5 mg, 75 mg, 225 mg or 750 mg, optionally administered every two weeks. In certain embodiments, a dose (e.g. each dose) of the anti-PD-1 antibody is administered at 1-20 mg/kg, optionally at 10 mg/kg. In certain embodiments, a dose (e.g. each dose) of the anti-PD-L1 antibody (e.g. durvalumab) is administered at 10, 15, 20 or 25 mg/kg, optionally at 750 mg total dose, optionally at 1500 mg total dose optionally administered every 4 weeks. In certain embodiments, the combined therapy permits the anti-PD-1 or PD-L1 antibody to be administered at a lower dose.

In one embodiment, the anti-NKG2A antibody and anti-PD-1 or anti-PD-L1 antibody are administered at the following doses:
(a) 0.1-10 mg/kg anti-NKG2A antibody and (i) 1-10 mg/kg of anti-PD-1 antibody or (ii) 1-20 mg/kg of anti-PD-L1 antibody;
(b) 1-10 mg/kg anti-NKG2A antibody and (i) 1-10 mg/kg of anti-PD-1 antibody or (ii) 1-20 mg/kg of anti-PD-L1 antibody;
(c) 225 mg anti-NKG2A antibody (e.g. monalizumab) and 750 mg/kg of anti-PD-L1 antibody (e.g. durvalumab);
(d) 750 mg anti-NKG2A antibody (e.g. monalizumab) and 750 mg/kg of anti-PD-L1 antibody (e.g. durvalumab);
(e) 225 mg anti-NKG2A antibody (e.g. monalizumab) and 1500 mg/kg of anti-PD-L1 antibody (e.g. durvalumab); or
(f) 750 mg anti-NKG2A antibody (e.g. monalizumab) and 1500 mg/kg of anti-PD-L1 antibody (e.g. durvalumab).

In one aspect of any of the embodiments herein, the anti-NKG2A antibody is administered once about every two weeks, optionally once every four weeks. In one aspect of any of the embodiments herein, the anti-PD-1 or anti-PD-L1 antibody is administered once about every four weeks.

In one embodiment the anti-PD-1 or anti-PD-L1 antibody and/or the anti-NKG2A antibody are administered by i.v. In one embodiment the anti-PD-1 or anti-PD-L1 antibody is administered every four weeks and the anti-NKG2A antibody is administered every two weeks, wherein every four weeks the anti-PD-1 or anti-PD-L1 antibody and NKG2A antibody are administered on the same day, optionally further by i.v.

In one embodiment, provided is a method for assessing whether an individual is suitable for treatment with an agent that inhibits NKG2A (and optionally further an agent that neutralizes the inhibitory activity of human PD-1), the method comprising assessing tumor DNA mismatch repair status in a biological sample from an individual. A determination that the individual has a tumor that is not DNA mismatch repair defective indicates that the patient has a cancer that can be treated with an agent that inhibits NKG2A, optionally further in combination with an agent that neutralizes the inhibitory activity of human PD-1. In one embodiment, the method is used to assess whether an individual is suitable for treatment with an agent that inhibits NKG2A and an agent that neutralizes the inhibitory activity of human PD-1 administered according to the administration regimens disclosed herein.

In another aspect, provided is a method of reducing the risk of cancer progression, reducing the risk of further cancer in CRC, optionally mCRC, and/or providing a therapeutic regimen for reducing cancer progression in a human individual, which comprises administering to the patient an amount of a NKG2A-neutralizing agent and a PD-1 neutralizing agent in a dosage and frequency according to the disclosure. In a further aspect, provided is a method of promoting remission of a cancer in an individual, such as a human patient, in particular a colorectal cancer, comprising administering a pharmaceutical composition comprising a NKG2A-neutralizing agent and a PD-1 neutralizing agent, to the individual, in a dosage and frequency according to the disclosure, so as to promote cancer remission in the individual. In a further aspect, provided is a method of preventing recurrence of a cancer, in particular colorectal cancer, in an individual, such as a human patient, whose cancer is in remission following a preceding anti-cancer treatment, comprising administering to the individual a composition comprising a NKG2A-neutralizing agent and a PD-1 neutralizing agent, in a dosage and frequency according to the disclosure, so as to promote cancer remission in the individual. In a further aspect, provided is a method of increasing the likelihood of survival over a relevant period in a human patient diagnosed with cancer, in particular a colorectal cancer, comprising administering to the patient a pharmaceutical composition comprising a NKG2A-neutralizing agent and a PD-1-neutralizing agent. In another aspect, provided is a method for improving the quality of life of a cancer patient comprising administering to the patient a pharmaceutical composition comprising a NKG2A-neutralizing agent and a PD-1 neutralizing agent in an amount effective to improve the quality of life thereof. In a further aspect, methods described herein can be applied to significantly reduce the number of cancer cells in a human, such that, for example, the total number of cancer cells is reduced. In a related sense, provided is a method for killing (e.g. either directly or indirectly causing death of) cancer cells in a mammal, such as a human cancer patient, in particular colorectal cancer cells. In still other embodiments of the methods described herewith, said individual has a tumor that is not MSI-High (MSI-H) and/or not DNA mismatch repair (MMR) defective.

The NKG2A-neutralizing agent in combination with the PD-1 neutralizing agent can be administered in combined administration (co-administration) with one or more additional therapeutic agents or therapies.

EXAMPLES

Example 1: Dose Finding is a Phase 1 Multicenter, Open-Label, Single-Arm Dose-Escalation and Dose-Expansion Study of Durvalumab in Combination with Monalizumab A Phase 1, multicenter, open-label, single-arm dose-escalation and dose-expansion study of durvalumab in combination with monalizumab (see WHO Drug Information Vol. 30, No. 1, 2016; also referred to as IPH2201; antibody having the heavy chain of SEQ ID NO: 11 and a light chain of SEQ ID NO: 15) was conducted to evaluate the safety, tolerability, PK, immunogenicity, pharmacodynamics, and antitumor activity in adult subjects with selected advanced solid tumors. The study consisted of 2 parts: a dose escalation and a dose expansion.

Subjects received durvalumab and monalizumab via 2 separate IV infusions. Subjects received durvalumab and monalizumab until unacceptable toxicity, documentation of confirmed progressive disease (PD), or documentation of subject withdrawal for another reason.

Inclusion Criteria included:
1. Subjects must have histologic documentation of advanced recurrent or metastatic cancer.
2. Subjects must have received and have progressed or are refractory to at least one line of standard systemic therapy in the recurrent/metastatic setting, with selected advanced solid tumors.
3. Subjects must have at least one lesion that is measurable by RECIST v1.1

Exclusion Criteria were as follows:"
1. Prior treatment with immunotherapy agents. Prior treatment with antitumor vaccines may be permitted upon discussion with the medical monitor.
2. Prior participation in clinical studies that include durvalumab alone or in combination, where the study has registrational intent and the analyses for the primary endpoint have not yet been completed
3. Receipt of any conventional or investigational anticancer therapy within 4 weeks prior to the first dose of durvalumab and monalizumab
4. Any concurrent chemotherapy, immunotherapy, biologic or hormonal therapy for cancer treatment. Concurrent use of hormones for non-cancer-related conditions is acceptable. Local treatment of isolated lesions for palliative intent is acceptable beyond the DLT-evaluation period with prior consultation and in agreement with the medical monitor.
5. Current or prior use of immunosuppressive medication within 14 days before the first dose.

Subjects in sequential cohorts received durvalumab (1500 mg every 4 weeks (Q4W)) in combination with monalizumab at 1 of 4 planned dose levels (22.5, 75, 225, or 750 mg every 2 weeks (Q2W).

In the 15 patients treated with monalizumab plus durvalumab in escalation, there were no treatment-related adverse events (TRAEs) that led to discontinuations, no grade 3/4 TRAEs, no DLTs, and no deaths; MTD was not reached. Any grade TRAEs were observed in 12 patients (80%); most frequent was diarrhea (n=4). Safety in the 40 patients in expansion was similar to escalation: 19 patients (48%) had any grade TRAEs, 1 patient had a grade 3/4 TRAE (sepsis). PK of both drugs in combination showed no interactions. Monalizumab PK approached linearity at the highest dose level, which was thus chosen for expansion.

At the end of the dose-escalation part of the trial, the maximum tolerated dose (MTD) was not reached and Cohort 4 dosing of monalizumab (750 mg Q2W) and durvalumab (1500 mg Q4W) was deemed safe by the dose escalation committee (DEC). Those doses are then employed in the dose expansion part of the study which is currently on-going. A dose de-escalation cohort using doses of durvalumab 1500 mg Q4W and monalizumab 7.5 mg Q2W will be implemented if unacceptable toxicity is encountered at the first dose level.

Example 2: Responses in MSS Colorectal Cancer Patients Treated with Monalizumab and Durvalumab in a CRC Dose Expansion Part of a Phase I Clinical Study The dose-expansion part of the phase 1 study aims to recruit patients into four cohorts corresponding to cancers which are not adequately treated with current therapies. One of the cohorts included recurrent or metastatic MSS-CRC subjects. In the MSS-CRC cohort, all subjects needed to have a documented mutation test during screening and confirmed tumor locations from disease assessment for enrolment, and CRC cancers must not have a defective DNA mismatch repair (microsatellite instability), as documented by testing.

Defective DNA mismatch repair was defined by either: (i) High-frequency microsatellite instability with changes detected in 2 or more panels of microsatellite markers (BAT-25, BAT-26, NR-21, NR-24, or MONO-27), or (ii) Immunohistochemical analysis demonstrating absence of protein expression of any one or more of the following proteins: MLH1, MSH2, MSH6, or PMS2.

Subjects cohorts received durvalumab (1500 mg every 4 weeks (Q4W)) in combination with monalizumab at 750 mg every 2 weeks (Q2W).

Results showed that in in the MSS-CRC expansion cohort (58% of patients having received at least 3 lines of prior therapy, n=37 evaluable for efficacy), there were 3 confirmed Partial Response (PR) (including one patient whose response has improved from Partial Response to unconfirmed Complete Response) and 11 Stable Disease (SD), including 3 patients with tumor reduction who continued therapy for >200 days. The Disease Control Rate (DCR) at 16 weeks was 24%.

Percent change in tumor size from baseline and duration of treatment in MSS-CRC expansion cohort are represented in FIG. 1.

An update of the dose expansion part of the Phase I clinical study on monalizumab and durvalumab in CRC described above shows the results that follow.

Subjects cohorts received durvalumab (1500 mg every 4 weeks (Q4W)) in combination with monalizumab at 750 mg every 2 weeks (Q2W).

Results showed that in in the MSS-CRC expansion cohort (60% of patients having received at least 3 lines of prior therapy, n=39 evaluable for efficacy), there were 1 confirmed complete response, 2 confirmed Partial Response (PR) and 11 Stable Disease (SD) (Tables 1 and 2).

TABLE 1

Prior anti-cancer treatment-as treated population

|  | MSS-CRC<br>N = 40 |
|---|---|
| Number of prior regimens | |
| n | 40 |
| Mean | 3.7 |
| SD | 1.9 |
| Median | 3.0 |
| (Min, Max) | (1, 11) |
| Prior systemic therapy | 40 (100%) |
| Prior radiation | 13 (32.5%) |

TABLE 1-continued

Prior anti-cancer treatment-as treated population

| | MSS-CRC<br>N = 40 |
|---|---|
| Prior surgery | 32 (80.0%) |
| Prior bone marrow/stem cell transplant | 0 |
| Most recent line of therapy for recurrent/metastatic disease | |
| n | 40 |
| First line | 7 (17.5%) |
| Second line | 9 (22.5%) |
| Third line or greater | 24 (60%) |
| NA | 0 |

TABLE 2

Disease response in response evaluable population

| | MSS-CRC<br>N = 39 |
|---|---|
| Best Overall Response | |
| CR | 1 (2.6%) |
| PR | 2 (5.1%) |
| SD | 11 (28.2%) |
| Unconfirmed PR | 0 |
| PD | 22 (56.4%) |
| Non-evaluable | 1 (2.6%) |
| Not available | 2 (5.1%) |
| CR + PR (confirmed and unconfirmed) | 3 (7.7%) |
| 95% C.I. | (1.7%-21.9%) |
| CR + PR (ORR) | 3 (7.7%) |
| 95% C.I. | (1.7%-21.9%) |
| Time to Response (weeks) | 3 |
| Median time$^a$ | 8.1 |
| 95% Cl of Median Time$^a$ | (7.4-24.6) |

$^a$Median time to response, and median duration of response and median duration of disease control assessed via Kaplan-Meier methods.
Response evaluable population includes patients in the as-treated population who have at least one post-baseline disease assessment or discontinued due to death or disease progression prior to the first post-baseline disease assessment.

The Disease Control Rate (DCR) at 16 weeks was 31% and 18% at 24 weeks (Table 3).

TABLE 3

Disease response in response evaluable population

| | MSS-CRC<br>N = 39 |
|---|---|
| Min, Max | (7.4, 24.6) |
| Duration of Response (weeks) | 3 |
| Median time$^a$ | 16.1 |
| 95% Cl of Median Time$^a$ | (15.9-NE) |
| Min, Max | (15.9 – 56.4+) |
| CR + PR + SD ≥ 16 weeks (DCR16) | 12 (30.8%) |

TABLE 3-continued

Disease response in response evaluable population

| | MSS-CRC<br>N = 39 |
|---|---|
| 95% Cl | (17.0%-47.6%) |
| CR + PR + SD ≥ 24 weeks (DCR24) | 7 (17.9%) |
| 95% Cl | (7.5%-33.5%) |

$^a$Median time to response, and median duration of response and median duration of disease control assessed via Kaplan-Meier methods.
Response evaluable population includes patients in the as-treated population who have at least one post-baseline disease assessment or discontinued due to death or disease progression prior to the first post-baseline disease assessment.

The Median OS obtained thus far is encouraging, being of 10.6 months, which com-pares favourably to Lonsurf/TAS-102 median OS of 5.7 months (Mayer et al, 2015, N. Engl. J. Med. 372:1909-1919) or against regorafenib reported median OS of 6.4 months (Grothey et al, Lancet 2013, 381(9863): 303-312) in a similar population.

Figure 2:
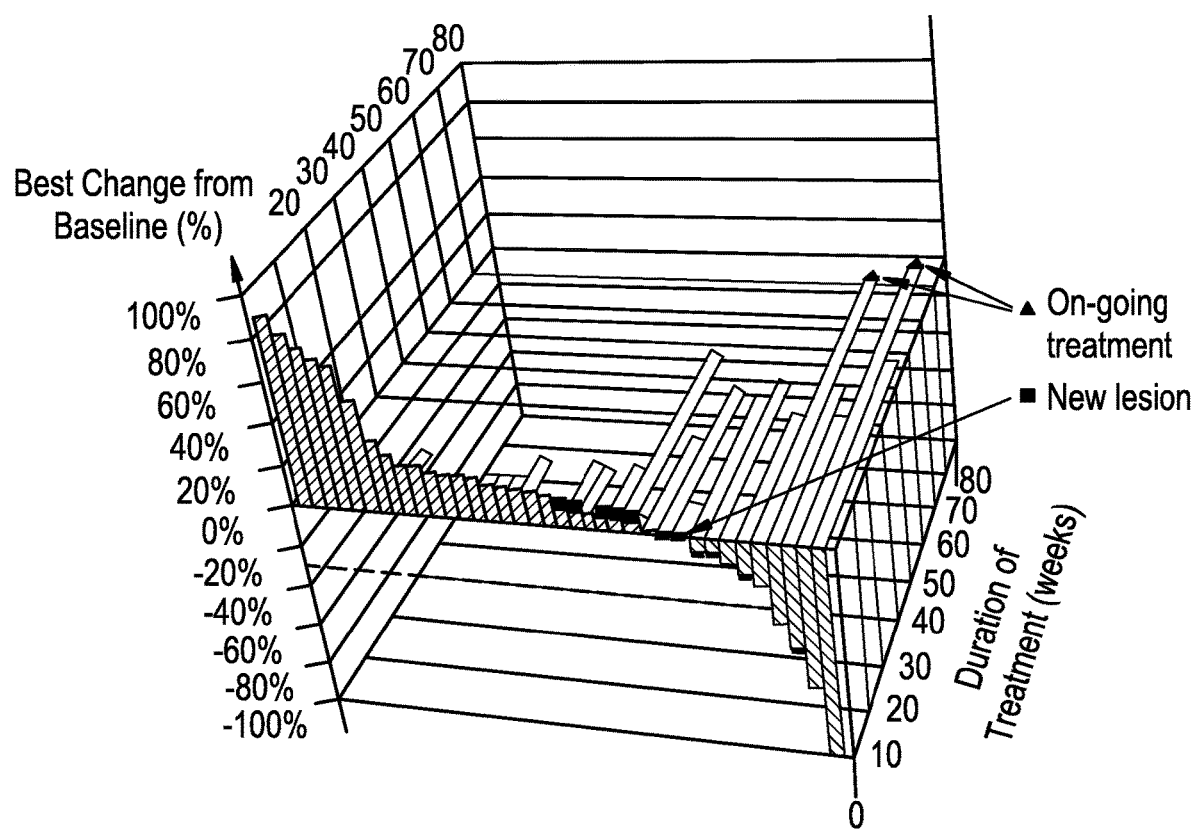
FIG. 2 is a 3D representation of the Best Change in Tumor Size from Baseline (in %, left-hand vertical axis) and Duration of Treatment Response in the Evaluable Population (in weeks, z axis) for each patient (horizontal axis) in the expansion cohort of the MSS-CRC trial on a longer time period compared to FIG. 1.

Percent change in tumor size from baseline and duration of treatment in this MSS-CRC expansion cohort are represented in FIG. 2, on a longer time period compared to FIG. 1.

In conclusion, dose escalation of this first-in-human combination of monalizumab plus durvalumab has been completed, demonstrating a manageable toxicity profile. The data indicate that the monalizumab plus durvalumab combination could bring an improved benefit to patients with MSS-CRC, a population historically nonresponsive to PD-1/PD-L1 blockade.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +/−10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

We claim:

1. A method of treating a cancer and/or eliciting an anti-tumor immune response in an individual in need thereof, wherein said individual has a tumor that is not MSI-High (MSI-H) and/or not DNA mismatch repair (MMR) defective, comprising administering to said individual a therapeutically effective amount of a NKG2A neutralizing agent and a therapeutically effective amount of a PD-1 neutralizing agent,
    wherein said individual has a cancer selected from the group consisting of colorectal cancer, recurrent colorectal cancer, metastatic colorectal cancer, colon cancer and rectal cancer,
    wherein said NKG2A neutralizing agent comprises the heavy chain H-CDR1, H-CDR2 and H-CDR3 domains having the sequences of SEQ ID NOS: 16-18, and the light chain L-CDR1, L-CDR2 and L-CDR3 domains having the sequences of SEQ ID NOS: 19-21, respectively, and
    wherein said PD-1 neutralizing agent comprises the heavy chain H-CDR1, H-CDR2 and H-CDR3 domains having the amino acid sequences of SEQ ID NOS: 28-30, and the light chain L-CDR1, L-CDR2 and L-CDR3 domains having the amino acid sequences of SEQ ID NOS: 31-33, respectively.

2. The method according to claim 1, wherein said individual has a tumor that does not have microsatellite instability detected in two or more microsatellite markers.

3. The method according to claim 1, wherein said individual has a tumor that does not have an alteration in expression of a DNA mismatch repair (MMR) protein.

4. The method according to claim 1, wherein said individual has a tumor that is microsatellite stable (MSS).

5. The method according to claim 1, wherein said individual has a colorectal cancer, an advanced recurrent colorectal cancer or a metastatic colorectal cancer.

6. The method according to claim 1, wherein said individual has a MSS-colorectal cancer (MSS-CRC).

7. The method according to claim 1, wherein said method comprises:
    a) a preliminary step of determining whether said individual has a tumor that is not MSI-H and/or DNA mismatch repair defective; and/or
    b) a preliminary step of determining whether said individual has a tumor that does not have an alteration in expression of a DNA mismatch repair (MMR) protein.

8. The method according to claim 1, wherein:
    a) said NKG2A neutralizing agent is an antibody that binds a human NKG2A protein, or
    b) said NKG2A neutralizing agent is a humanized anti-NKG2A antibody.

9. The method according to claim 1, wherein said NKG2A neutralizing agent is an antibody that inhibits binding of NKG2A to HLA-E.

10. The method according to claim 1, wherein said NKG2A neutralizing agent is monalizumab.

11. The method according to claim 1, wherein:
    a) said PD-1 neutralizing agent is an antibody that binds a human PD-L1 polypeptide; or
    b) said PD-1 neutralizing agent is a human anti-PD-L1 antibody.

12. The method according to claim 1, wherein said PD-1 neutralizing agent is durvalumab.

13. The method according to claim 1, wherein said NKG2A neutralizing agent is monalizumab and said PD-1 neutralizing agent is durvalumab.

14. The method according to claim 1, wherein said NKG2A neutralizing agent and said PD-1 neutralizing agent are formulated for separate administration and are administered concurrently or sequentially.

15. The method according to claim 1, wherein:
    a) said NKG2A neutralizing agent is administered at a dose ranging from 0.1 to 10 mg/kg and said PD-1 neutralizing agent is administered at a dose ranging from 1 to 20 mg/kg,
    b) said NKG2A neutralizing agent is administered at a dose of 10 mg/kg and said PD-1 neutralizing agent is administered at a dose of 20 mg/kg, or
    c) said NKG2A neutralizing agent is monalizumab administered at a fixed dose of 750 mg every 2 weeks and said PD-1 neutralizing agent is durvalumab administered at a fixed dose of 1500 mg every 4 weeks.

16. The method according to claim 2, wherein said individual has a tumor that has no alteration detected in two or more of the microsatellite markers selected from the group consisting of BAT-25, BAT-26, NR-21, NR-24, and MONO27.

17. The method according to claim 3, wherein said individual has a tumor that does not have decreased or absence of expression of at least one MMR protein selected from MSH2, MLH1, MSH6 and PMS2.

18. The method according to claim 7, wherein said method comprises:
  a) a preliminary step of determining whether said individual has a tumor that is not MSI-H and/or DNA mismatch repair defective, said determining comprising determining whether said individual has a tumor that does not have microsatellite instability detected in two or more microsatellite markers selected from the group consisting of BAT-25, BAT-26, NR-21, NR-24, and MONO27; and/or
  b) a preliminary step of determining whether said individual has a tumor that does not have an alteration in expression of a DNA mismatch repair (MMR) protein, said determining comprising whether said individual has a tumor that does not have decreased or absence of expression of at least one MMR protein selected from MSH2, MLH1, MSH6, and PMS2.

* * * * *

SEQUENCE LISTING

<160> NUMBER OF SEQ ID NOS: 38

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg

```
                    85                  90                  95
Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```

<210> SEQ ID NO 3
<211> LENGTH: 290
<212> TYPE: PRT
<213> ORGANISM: Homo sapiens

<400> SEQUENCE: 3

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 4
<211> LENGTH: 124
<212> TYPE: PRT
<213> ORGANISM: Artificial Sequence
<220> FEATURE:
<223> OTHER INFORMATION: VH6

<400> SEQUENCE: 4

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: VH1

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

```
Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120
```

<210> SEQ ID NO 6
<211> LENGTH: 124
<212> TYPE: PRT
<213> ORGANISM: Artificial Sequence
<220> FEATURE:
<223> OTHER INFORMATION: VH5

<400> SEQUENCE: 6

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Met Asn Trp Val Arg Gln Met Pro Gly Lys Gly Leu Glu Trp Met
            35                  40                  45

Gly Arg Ile Asp Pro Tyr Asp Ser Glu Thr His Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120
```

<210> SEQ ID NO 7
<211> LENGTH: 124
<212> TYPE: PRT
<213> ORGANISM: Artificial Sequence
<220> FEATURE:
<223> OTHER INFORMATION: VH7

<400> SEQUENCE: 7

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
                20                  25                  30

Trp Met Asn Trp Val Gln Gln Ala Pro Gly Lys Gly Leu Glu Trp Met
            35                  40                  45

Gly Arg Ile Asp Pro Tyr Asp Ser Glu Thr His Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser
```

-continued

```
                115                 120

<210> SEQ ID NO 8
<211> LENGTH: 124
<212> TYPE: PRT
<213> ORGANISM: Artificial Sequence
<220> FEATURE:
<223> OTHER INFORMATION: VH8

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
        115                 120

<210> SEQ ID NO 9
<211> LENGTH: 107
<212> TYPE: PRT
<213> ORGANISM: Artificial Sequence
<220> FEATURE:
<223> OTHER INFORMATION: Light chain variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105

<210> SEQ ID NO 10
<211> LENGTH: 452
<212> TYPE: PRT
<213> ORGANISM: Artificial Sequence
<220> FEATURE:
<223> OTHER INFORMATION: VH6 heavy chain

<400> SEQUENCE: 10

Glu Val Gln Leu Val Gln Ser Gly Ala Glu Val Lys Lys Pro Gly Glu
1               5                   10                  15
```

-continued

```
Ser Leu Lys Ile Ser Cys Lys Gly Ser Gly Tyr Ser Phe Thr Ser Tyr
             20                  25                  30

Trp Met Asn Trp Val Arg Gln Met Pro Gly Lys Gly Leu Glu Trp Met
         35                  40                  45

Gly Arg Ile Asp Pro Tyr Asp Ser Glu Thr His Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Gly Gly Tyr Asp Phe Asp Val Gly Thr Leu Tyr Trp Phe Phe
        100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430
```

Met His Glu Ala Leu His Asn His Tyr Thr Gln Lys Ser Leu Ser Leu
            435                 440                 445

Ser Leu Gly Lys
        450

<210> SEQ ID NO 11
<211> LENGTH: 452
<212> TYPE: PRT
<213> ORGANISM: Artificial Sequence
<220> FEATURE:
<223> OTHER INFORMATION: VH1 heavy chain

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

```
Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
        450

<210> SEQ ID NO 12
<211> LENGTH: 452
<212> TYPE: PRT
<213> ORGANISM: Artificial Sequence
<220> FEATURE:
<223> OTHER INFORMATION: VH5 heavy chain

<400> SEQUENCE: 12

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

Gln Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 13
<211> LENGTH: 452
<212> TYPE: PRT
<213> ORGANISM: Artificial Sequence
<220> FEATURE:
<223> OTHER INFORMATION: VH7 heavy chain

<400> SEQUENCE: 13

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
        35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140
```

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
    195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

Gln Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
    435                 440                 445

Ser Leu Gly Lys
    450

<210> SEQ ID NO 14
<211> LENGTH: 452
<212> TYPE: PRT
<213> ORGANISM: Artificial Sequence
<220> FEATURE:
<223> OTHER INFORMATION: VH8 heavy chain

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

```
Gly Arg Ile Asp Pro Tyr Asp Ser Glu Thr His Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
450
```

```
<210> SEQ ID NO 15
<211> LENGTH: 214
<212> TYPE: PRT
<213> ORGANISM: Artificial Sequence
<220> FEATURE:
<223> OTHER INFORMATION: Light chain

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 5
<212> TYPE: PRT
<213> ORGANISM: Artificial Sequence
<220> FEATURE:
<223> OTHER INFORMATION: H-CDR1

<400> SEQUENCE: 16

Ser Tyr Trp Met Asn
1               5

<210> SEQ ID NO 17
<211> LENGTH: 17
<212> TYPE: PRT
<213> ORGANISM: Artificial Sequence
<220> FEATURE:
<223> OTHER INFORMATION: H-CDR2

<400> SEQUENCE: 17

Arg Ile Asp Pro Tyr Asp Ser Glu Thr His Tyr Ala Gln Lys Leu Gln
1               5                   10                  15

Gly
```

```
<210> SEQ ID NO 18
<211> LENGTH: 16
<212> TYPE: PRT
<213> ORGANISM: Artificial Sequence
<220> FEATURE:
<223> OTHER INFORMATION: H-CDR3

<400> SEQUENCE: 18

Gly Gly Tyr Asp Phe Asp Val Gly Thr Leu Tyr Trp Phe Phe Asp Val
1               5                   10                  15

<210> SEQ ID NO 19
<211> LENGTH: 11
<212> TYPE: PRT
<213> ORGANISM: Artificial Sequence
<220> FEATURE:
<223> OTHER INFORMATION: L-CDR1

<400> SEQUENCE: 19

Arg Ala Ser Glu Asn Ile Tyr Ser Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: L-CDR2

<400> SEQUENCE: 20

Asn Ala Lys Thr Leu Ala Glu
1               5

<210> SEQ ID NO 21
<211> LENGTH: 9
<212> TYPE: PRT
<213> ORGANISM: Artificial Sequence
<220> FEATURE:
<223> OTHER INFORMATION: L-CDR3

<400> SEQUENCE: 21

Gln His His Tyr Gly Thr Pro Arg Thr
1               5

<210> SEQ ID NO 22
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 22

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Ser Pro Glu Lys Arg Leu Glu Trp Val
            35                  40                  45

Ala Glu Ile Ser Ser Gly Gly Ser Tyr Thr Tyr Tyr Pro Asp Thr Val
        50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95
```

```
Thr Arg His Gly Asp Tyr Pro Arg Phe Phe Asp Val Trp Gly Ala Gly
            100                 105                 110

Thr Thr Val Thr Val Ser Ser
        115
```

<210> SEQ ID NO 23
<211> LENGTH: 106
<212> TYPE: PRT
<213> ORGANISM: Artificial Sequence
<220> FEATURE:
<223> OTHER INFORMATION: Light chain variable region

<400> SEQUENCE: 23

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Ile
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys
            100                 105
```

<210> SEQ ID NO 24
<211> LENGTH: 121
<212> TYPE: PRT
<213> ORGANISM: Artificial Sequence
<220> FEATURE:
<223> OTHER INFORMATION: Heavy chain variable region of Durvalumab

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
            115                 120
```

<210> SEQ ID NO 25
<211> LENGTH: 108
<212> TYPE: PRT
<213> ORGANISM: Artificial Sequence
<220> FEATURE:
<223> OTHER INFORMATION: Light chain variable region of Durvalumab

```
<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 26
<211> LENGTH: 451
<212> TYPE: PRT
<213> ORGANISM: Artificial Sequence
<220> FEATURE:
<223> OTHER INFORMATION: Heavy chain of Durvalumab

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240
```

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 27
<211> LENGTH: 215
<212> TYPE: PRT
<213> ORGANISM: Artificial Sequence
<220> FEATURE:
<223> OTHER INFORMATION: Light chain of Durvalumab

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 28
<211> LENGTH: 10
<212> TYPE: PRT
<213> ORGANISM: Artificial Sequence
<220> FEATURE:
<223> OTHER INFORMATION: H-CDR1

<400> SEQUENCE: 28

Gly Phe Thr Phe Ser Arg Tyr Trp Met Ser
1               5                   10

<210> SEQ ID NO 29
<211> LENGTH: 17
<212> TYPE: PRT
<213> ORGANISM: Artificial Sequence
<220> FEATURE:
<223> OTHER INFORMATION: H-CDR2

<400> SEQUENCE: 29

Asn Ile Lys Gln Asp Gly Ser Glu Lys Tyr Tyr Val Asp Ser Val Lys
1               5                   10                  15

Gly

<210> SEQ ID NO 30
<211> LENGTH: 12
<212> TYPE: PRT
<213> ORGANISM: Artificial Sequence
<220> FEATURE:
<223> OTHER INFORMATION: H-CDR3

<400> SEQUENCE: 30

Glu Gly Gly Trp Phe Gly Glu Leu Ala Phe Asp Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: L-CDR1

<400> SEQUENCE: 31

Arg Ala Ser Gln Arg Val Ser Ser Ser Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: L-CDR2

<400> SEQUENCE: 32

Asp Ala Ser Ser Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: L-CDR3

<400> SEQUENCE: 33

Gln Gln Tyr Gly Ser Leu Pro Trp Thr
1               5

<210> SEQ ID NO 34
<211> LENGTH: 118
<212> TYPE: PRT
<213> ORGANISM: Artificial Sequence
<220> FEATURE:
<223> OTHER INFORMATION: heavy chain variable region

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 35
<211> LENGTH: 122
<212> TYPE: PRT
<213> ORGANISM: Artificial Sequence
<220> FEATURE:
<223> OTHER INFORMATION: heavy chain variable region

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr

Leu Val Thr Val Ser Ser Ala Ser Thr Lys
        115                 120

<210> SEQ ID NO 36
<211> LENGTH: 108
<212> TYPE: PRT
<213> ORGANISM: Artificial Sequence
<220> FEATURE:
<223> OTHER INFORMATION: light chain variable region

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 37
<211> LENGTH: 445
<212> TYPE: PRT
<213> ORGANISM: Artificial Sequence
<220> FEATURE:
<223> OTHER INFORMATION: heavy chain

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 38
<211> LENGTH: 213
<212> TYPE: PRT
<213> ORGANISM: Artificial Sequence
<220> FEATURE:
<223> OTHER INFORMATION: light chain

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```